US008114914B2

(12) United States Patent
Fahl et al.

(10) Patent No.: US 8,114,914 B2
(45) Date of Patent: *Feb. 14, 2012

(54) TOPICAL VASOCONSTRICTOR PREPARATIONS AND METHODS FOR PROTECTING CELLS DURING CANCER CHEMOTHERAPY AND RADIOTHERAPY

(75) Inventors: William E. Fahl, Madison, WI (US); Arnold E. Ruoho, Madison, WI (US); Minesh Mehta, Sun Prairie, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1473 days.

This patent is subject to a terminal disclaimer.

(21) Appl. No.: 11/471,047

(22) Filed: Jun. 19, 2006

(65) Prior Publication Data

US 2007/0077219 A1    Apr. 5, 2007

Related U.S. Application Data

(60) Provisional application No. 60/691,571, filed on Jun. 17, 2005.

(51) Int. Cl.
| A61K 31/05 | (2006.01) |
| A61K 31/045 | (2006.01) |
| A61K 31/164 | (2006.01) |
| A61K 31/4174 | (2006.01) |
| A61K 31/4196 | (2006.01) |
| A61K 31/496 | (2006.01) |
| A61K 31/422 | (2006.01) |

(52) U.S. Cl. .................. 514/728; 514/252.14; 514/376; 514/383; 514/396

(58) Field of Classification Search .................. None
See application file for complete search history.

(56) References Cited

U.S. PATENT DOCUMENTS

| 2,774,789 | A | * | 12/1956 | Tullar | 562/585 |
| 2,919,230 | A | * | 12/1959 | Thurmon | 424/78.05 |
| 5,256,652 | A | * | 10/1993 | El-Rashidy | 514/58 |
| 7,314,959 | B2 | * | 1/2008 | Fahl et al. | 564/512 |
| 2005/0101676 | A1 | * | 5/2005 | Fahl et al. | 514/665 |

FOREIGN PATENT DOCUMENTS

WO    WO 2005/014524 A2    2/2005

OTHER PUBLICATIONS 1999-2000 Drug Information Handbook, Lacy, C.; Armstrong, L. L.; Lipsy, R. J.; Lance, L. L. Drug Information Handbook, Lexi-Comp, Inc.: Cleveland, 1999, pp. 323-324, 715-716, 742-743, and 1026-1028.*
Wikipedia entry, "Vasoconstriction" accessed on Jan. 16, 2010 at en.wikipedia.org/wiki/Vasoconstrictor.*
Merck Online Home Edition Medical Library Article, "Dermatitis"—accessed on Jan. 16, 2010 at www.merck.com/mmhe/print/sec18/ch203/ch203c.html.*
Solomon et al. "Studies in the mechanism of steroid vasoconstriction." J. Invest. Dermatol., 1965, 44(3), Abstract only.*
Merck Online Home Edition Medical Library Article, "Shock"—accessed on Jan. 16, 2010 at www.merck.com/mmhe/print/sec03/ch024/ch024a.html.*
González et al. ("The phototoxicity of photodynamic therapy may be suppressed or enhanced by modulation of the cutaneous vasculature," Journal of Photochemistry and Photobiology B: Biology, 2000, 50, pp. 142-148.*
Merck Online Home Edition Medical Library Article, "Alopecia"—accessed on Sep. 3, 2010 at www.merck.com/mmhe/print/sec18/ch207/ch207c.html.*
Principles and Practice of Dermatology, $2^{nd}$ edition, W. Mitchell Sams, J.R., M.D. and Peter J. Lynch, M.D., eds., Churchill-Livingstone: New York, 1996, pp. 1-3.*
Pharmaceutical Dosage Forms and Drug Delivery Systems, 7th edition, Howard C. Ansel, Loyd V. Allen, and Nicholas G. Popovich, eds., Lippincott Williams & Wilkins: Baltimore, 1999, pp. 89 and 244-246.*
Alvarez, E., et al., "Preclinical Characterization of CG53135 (FGF-20) in Radiation and Concomitant Chemotherapy . . . ," Clinical Cancer Research 9:3454-3461 (2003).
Davis, S.T., et al., "Prevention of Chemotherapy-Induced Alopecia in Rats by CDK Inhibitors," Science 291:134-137(2001).
Badvie, S. et al., Topical Phenylephrine in the Treatment of Radiation-induced Faecal Incontinence, Clinical Oncology (2005) 17: 122-126.
Gao et al., (1996) Radioprotective Effect of Epinephrine as a Vasoconstrictor in Mouse Oral Mucosa and Scalp, *Okayama Igakkai Zasshi*, 108:139-144.
Vasin et al., (1999) Radiation protective efficacy of alpha-adrenomimetics during local gamma irradiation of the skin, *Radiats Biol Radioecol.*, 39(2-3):249-53.

* cited by examiner

*Primary Examiner* — James H Alstrum Acevedo
(74) *Attorney, Agent, or Firm* — Joseph T. Leone, Esq.; DeWitt Ross & Stevens S.C.

(57) ABSTRACT

Vasoconstrictors are administered topically to provide protection against the adverse effects, e.g., alopecia, mucositis or dermatitis, induced by chemotherapy or radiotherapy. Appropriate dosages and formulations of topical vasoconstrictors are provided. Methods for the use of such compositions are also provided.

39 Claims, 14 Drawing Sheets

Arrows designate cross-section of follicles showing dye distribution throughout follicle

TOPICAL VASOCONSTRICTOR PREPARATIONS AND METHODS FOR PROTECTING CELLS DURING CANCER CHEMOTHERAPY AND RADIOTHERAPY

CROSS-REFERENCE TO RELATED APPLICATIONS

This claims priority to U.S. Provisional Patent Application No. 60/691,571, filed Jun. 17, 2005, which is incorporated in its entirety herein by reference.

Pursuant to 35 U.S.C. §202 (c), it is acknowledged that the United States Government has certain rights in the invention described herein, which was made in part with funds from the National Institutes of Health, Grant No. CA22484.

FIELD OF THE INVENTION

The present invention relates to the field of cancer therapy. In particular, the invention provides pharmaceutical preparations and methods for protecting non-neoplastic cells from the toxic side-effects of radiotherapy and cancer chemotherapeutic agents using vasoconstrictor molecules.

BACKGROUND OF THE INVENTION

The use of chemotherapy and radiotherapy to treat cancer patients is associated with severe side-effects due to the toxicity of such treatments to normal cells, particularly epithelial cell populations, including stem cells, within the hair follicle, skin epidermis, and gastrointestinal mucosa.

Currently, there are few, if any, treatments to prevent cancer therapy side-effects. The full utility of chemotherapeutic drugs and radiation therapy (also referred to herein as "radiotherapy") in the treatment of cancer has not been fully exploited due to adverse effects associated with the nonspecific cytotoxicity of these agents.

Effective treatments would preferably include: i) a means to decrease the concentration of systemically administered cytotoxic drugs in at-risk stem cells of the skin epidermis, hair follicles and gastrointestinal mucosa, and ii) a means to transiently decrease the concentration of oxygen in at-risk stem cells of the skin epidermis, hair follicles and gastrointestinal mucosa, because the majority of radiation-induced cell kill in tissue results from radiation-induced oxygen free radicals.

The toxicity of cancer therapy for epithelial cells accounts for many of the side-effects commonly suffered by persons undergoing a regimen of chemotherapy or radiotherapy. These include gastrointestinal distress, nausea, vomiting, diarrhea, proctitis, loss of appetite, hair loss, bone marrow suppression and skin rash or ulceration at the site of irradiation. These complications can be so difficult to endure that patients may forego or discontinue recommended cancer therapy treatments in order to avoid the side-effects. Typically, during the course of chemotherapy, the chemotherapeutic agent is administered in sub-optimal doses in order to minimize toxicity and to protect normal, drug-sensitive cells.

For example, gastrointestinal disturbances may compromise a patient's chances of recovery because they make it difficult for the patient to obtain the nourishment necessary to optimize their ability to fight disease. It appears that chemo- and radiotherapy-associated death and sloughing of gastrointestinal lumenal cells results in release into the vasculature of molecules associated with gastrointestinal damage. These blood-borne molecules, when detected by sites within the brain, trigger a nausea response that is so common among patients receiving chemotherapy. Present treatments with drugs, such as Ondansetron, serve to suppress these brain centers and thus, diminish the nausea response. However, the primary destruction of the gastrointestinal lining still limits the most effective use of chemotherapy.

A better mechanism to diminish nausea in these patients would be to eliminate the primary destruction of the gastrointestinal surface and thereby prevent the release of damage-associated, nausea-inducing molecules, rather than just suppressing the effects of these molecules in the brain. Reducing the sensitivity of normal cells to chemotherapeutic agents would allow the administration of higher drug dosages and render the chemotherapy more effective.

Radiation-induced dermatitis is another recognized side effect of cancer treatment. Radiotherapy is used regularly as a primary or adjunct therapy for cancer patients, but dermatitis or scorched skin within the irradiated field is a common and painful side effect in the majority of radiation therapy patients Mucositis is an also important and costly side-effect of cancer therapy. As an inflammation of a mucosal surface, mucositis is a frequent, potentially severe complication of chemotherapy and/or radiotherapy. It can manifest as erythema, desquamation, ulcer formation, bleeding and exudate. It is generally accepted that mucositis results from the direct inhibitory effects of chemotherapy or radiotherapy on DNA replication and mucosal stem cell proliferation. These events result in reduction in the regeneration capability of the basal epithelium, leading to mucosal atrophy, collagen breakdown, and ulceration. A secondary effect is infection from a number of pathogens after the breakdown of the protective mucosal barrier.

Mucositis can be present throughout the gastrointestinal and urogenital tract, from the oral cavity to the intestines and rectum. It is particularly debilitating because it can lead to abnormal nutrition, increased systemic infections, use of narcotics to diminish pain, and postponement of cancer therapy. No commercial drugs are known to prevent mucositis due to cancer therapy. Present treatments for oral mucositis include application of basic principles of oral hygiene, and therapies, such as topical anesthetics and systemic analgesics to relieve pain, are used in an effort to minimize the symptoms. Auxiliary measures to protect normal cells of the gastrointestinal tract involve nutrient stimulation and maximizing the intake of growth factors. However, those therapies also do not address the underlying cause of mucositis.

The successful implementation of protective therapies that promote routine growth and proliferation of normal cells in the presence of radiotherapy or chemotherapeutic agents will permit the use of higher dose, more aggressive cancer therapy. Consequently, these protective therapies may not only address the side-effects of cancer and its treatment, but may enable greater treatment efficacy against cancer than is seen using current therapies.

Two useful targets for development of protective therapies are (1) epithelial cells, such as those lining the oral and entire gastrointestinal or urogenital tract, and (2) other epithelial cells, for example those of the skin, including hair follicles and the epidermis. The effectiveness and utility of existing approaches is limited, underscoring the requirement for new effective therapies to alleviate these side-effects.

There is, therefore, need for safe and effective drug preparations that can reduce the side-effects of cancer treatment, for example mucositis, and methods for reducing or minimizing these side-effects. More specifically, there exists a need to provide methods for topical administration of a vasoconstrictor to at-risk, non-neoplastic tissues, and by so doing, reduce delivery of systemic chemotherapy and cause transient hypoxia to reduce oxygen free-radical formation during radiation therapy There is also a need to provide topical vasoconstrictor preparations, which by design as to dose, delivery vehicle formulation, and vasoconstrictor receptor specificity, provide protection, especially local protection, to at-risk, non-neoplastic cells against cancer therapy side-effects, but reduce or even prevent one or more unwanted systemic effects of the applied vasoconstrictor.

There is also a need to provide preparations that enable topical, oral administration of a vasoconstrictor in a formulation whose flavor is well tolerated by cancer patients.

There is also a need for methods of treatment that comprise the application of an effective but non-toxic dose of vasoconstrictor combined with topical delivery vehicles that facilitate delivery to the skin or mucosal surfaces of a human or animal cancer patient.

SUMMARY OF THE INVENTION

The present invention relates to topically-applied pharmaceutical preparations and methods for preventing the side-effects of cancer therapy. More specifically, this invention relates to delivery of vasoconstrictor molecules to protect noncancerous epithlelial cells in the skin, hair follicles, and mucous membranes of the gastrointestinal and urogenital tracts of cancer patients from side-effects which occur as a result of cancer chemotherapy and/or radiotherapy.

In one of its several aspects, the invention provides methods for reducing a condition that results from the side-effects of therapy in a patient. The methods comprise administering a preparation comprising a vasoconstrictor in a pharmaceutically-acceptable delivery vehicle in an amount effective to reduce side-effects of a therapy such as treatment with one or more chemotherapeutic agents, radiation therapy, or a combination thereof. In various preferred embodiments, the condition caused by the side-effect comprise one or more of alopecia, dermatitis, mucositis, gastrointestinal distress, or proctitis.

In one embodiment, the conditions related to the side-effects are reduced in one or more non-neoplastic cells of the skin, scalp, mouth, rectum, nasoesophageal system, gastrointestinal system, or urogenital system. In certain embodiments, the preparation is administered prophylatically, e.g. either prior to the initiation of the chemo-, radio- or combination therapy, or before the onset of causative damage that manifests the side-effects. Certain presently preferred embodiments are directed at mucositis and proctitis, two common and problematic side-effects of such therapy. In certain embodiments, the preparation is formulated with a delivery vehicle to optimize delivery of the vasoconstrictor to cells of the targeted mucosa—for example to the rectum or rectal mucosa for proctitis, and the oral mucosa for mucositis (e.g. oral mucositis).

As discussed in more detail below, presently preferred vasoconstrictors for use in the methods and with the preparations of the invention include but are not limited to epinephrine, phenylephrine, methoxamine, norepinephrine, zolmitriptan, tetrahydrozaline, and naphazoline, as well as combinations thereof. It will be appreciated by the skilled artisan that combinations of the foregoing are useful and as such, are within the scope of the invention. Presently preferred α adrenergic receptor antagonists for use with the various embodiments invention include but are not limited to prazosin, doxazosin, terazosin, alfuzosin, tamsulosin, and combinations thereof.

In another embodiment, the methods further comprise administering after the therapy, an effective amount of a second preparation comprising an α adrenergic receptor antagonist in a pharmaceutically-acceptable delivery vehicle for delivering the compound to cells receiving the vasoconstrictor-containing preparation. Such methods are useful for alleviating affects associated with exposure of sensitive cell type to vasoconstrictors. Preferably such antagonists are administered with a component, for example the delivery vehicle, that has moisturizing or lubricating properties to provide further relief from any drying effect of the vasoconstrictor(s).

In another aspect of the invention, pharmaceutical preparations are provided for protecting cells in a patient from toxic effects of a therapy, such as with chemotherapeutic agents or radiation. The preparation comprises at least one vasoconstrictor and a pharmaceutically-acceptable delivery vehicle suitable for delivering the vasoconstrictor to the vasculature serving the cell. In other embodiments the preparation also comprises one or more additives, such as flavoring agents to improve the palatability of the preparations for oral administration to subjects. In preferred embodiments, the vasoconstrictor is epinephrine, phenylephrine, methoxamine, norepinephrine, zolmitriptan, tetrahydrozaline, or naphazoline, or combinations thereof.

In some embodiments, the preparations comprise epinephrine. Preferably the concentration is between about 5 mM and about 1500 mM, and more preferably between about 100 mM and about 1500 mM. Also preferred are compositions having between about 5 and about 100 mM, between about 50-250 mM, between about 100 mM-1000 mM, or even 1500 nM. Alternatively, certain embodiments utilize between about 0.009% and about 11% epinephrine. Also preferred are compositions having between about 0.009% and about 0.9%, between about 0.1% and about 0.5%, between about 0.5% and about 11%, and from about 1.1% to about 11%.

In other embodiments the pharmaceutical preparation comprises phenylephrine, preferably in concentration of between about 10 mM and about 5000 mM, and preferably between about 250 mM and about 5000 mM. Also preferred are compositions having between about 10-100 mM, 50-250 mM, 100-500 mM, and 250-2500 mM, or more. Compositions having between about 0.03% and about 25% phenylephrine are also useful herein. Also preferred are those preparations having between about 0.03% and 0.22%, between about 0.20% and about 1.5%, between about 1.5% and about 5%, and between about 5% and about 25%.

In other embodiments the pharmaceutical preparation comprises norepinephrine, preferably in concentration of between about 4.5 mM and about 1500 mM, and preferably between about 100 mM to about 1500 mM. Other preferred ranges include between about 4.5-50 mM, 40-100 mM, 75-250 mM, 10-500 mM, 200-800 mM, or 100-1500 mM or more.

In another embodiment, the pharmaceutical preparation comprises methoxamine, preferably in concentrations of between about 10 mM and about 5000 mM, and preferably between about 250 mM and about 5000 mM. Other preferred ranges include between about 10-100 mM, 50-250 mM, 200-1000 mM, 250-2500 mM or more. Alternatively, compositions include between about 0.01% and about 25%. Also preferred are preparation with between about 0.01% and about 0.5%, about 0.5% and 1%, and greater than about 1% up to about 25%.

In another embodiment, the pharmaceutical preparations of the invention further comprising a free radical scavenger. This particularly useful where oxidative damage is caused by free radical formation induced by the therapy.

In another embodiment, the pharmaceutical preparations include one or more pharmaceutically acceptable delivery vehicles comprising liposomes, a lipid droplet emulsion, an oil, an aqueous emulsion of polyoxyethylene ethers, an aqueous alcohol mixture, an aqueous ethanol mixture containing propylene glycol, a pharmaceutically acceptable gum in aqueous buffer, a modified cellulose in aqueous buffer, a modified cellulose in an alcohol-aqueous buffer mixture, a modified cellulose in an alcohol-aqueous buffer-propylene glycol mixture, or diethylene glycol monoethyl ether in aqueous buffer. Presently preferred are aqueous alcohol mixtures, and aqueous ethanol mixtures containing propylene glycol. Also preferred are modified cellulose-based delivery vehicles, particularly hydroxypropymethylcellulose, for example in an alcohol-aqueous buffer-propylene glycol mixture.

In other of its aspects, the invention provides methods wherein the vasoconstrictor is present in an amount effective for transiently constricting dermal blood vessels to reduce the amount of systemic chemotherapy arriving at cells, preferably stem cells, within the epidermis or hair follicle. In other embodiments the concentration of vasoconstrictor is sufficient for transiently constricting dermal blood vessels to reduce the amount of oxygenated blood arriving at stem cells within the epidermis or hair follicle. In certain embodiments, blood vessels are transiently restricted so as to reduce the amount of chemotherapy locally in the vicinity of such stem cells, and the amount of oxygenated blood is also reduced. In other embodiments, the vasoconstrictor is present in an amount effective for transiently constricting dermal blood vessels to reduce the amount of systemic chemotherapy present within the dermal vasculature and arriving at stem cells within the oral mucosa, or transiently constricting dermal blood vessels to reduce the amount of oxygenated blood present within the dermal vasculature and arriving at stem cells within the oral mucosa.

In another embodiment, the topical preparation for skin is formulated to provide a prophylactic dose of epinephrine that is effective in preventing radiation therapy-induced dermatitis or chemotherapy- or radiation therapy-induced alopecia, but low enough to minimize or avoid necrotizing local toxicity or skin pass-through of the epinephrine that might result in undesired systemic, or cardiac side-effects.

In a further embodiment, the topical delivery vehicle is specifically formulated for skin, preferably to enable vasoconstrictor penetration of the stratum corneum and access to underlying, dermal vasculature that serves epidermal and hair follicle stem cells, but to eliminate or limit vasoconstrictor distribution beyond the skin and hair follicles. Preferably the vasoconstrictor distribution remains relatively local to the site of application.

In a further embodiment, the vasoconstrictor selected can confer constriction of skin or mucosal vasculature, but does not pose any substantial risk of undesired cardiac side-effects seen with dual α and β adrenergic agonists like epinephrine. In one presently preferred embodiment, α1 adrenergic receptor-specific agonists are used as the topically-applied vasoconstrictor. Without limiting the invention to any particular theory of operation, such vasoconstrictors may offer useful properties because they are highly selective agonists. It will be appreciated by those skilled in the art that the undesirable cardiac side effects of dual α and β adrenergic agonists like epinephrine are due to interactions at the β2 receptor, which affects cardiac rate. Presently preferred examples of α1 adrenergic receptor-specific agonists for use in various embodiments of the invention are phenylephrine and methoxamine. A presently preferred example of a less selective α1 adrenergic receptor-specific that is also a β1 adrenergic receptor-specific agonist but not a β2 adrenergic receptor-specific agonist is norepinephrine. Combinations of the foregoing are also contemplated for use herein.

In another embodiment of the invention, the topical preparation is formulated to reduce or preferably prevent oral mucositis in cancer patients receiving radiation therapy or systemic chemotherapy, or a combination of therapies together, or sequentially. The preparation is formulated to provide a minimal dose of epinephrine, phenylephrine, norepinephrine, or methoxamine, or a combination thereof, that reduces or completely prevents oral mucositis. Preferably the formulation is also formulated with doses of epinephrine, phenylephrine, norepinephrine, or methoxamine, or combination thereof, that do not induce any significant, necrotizing toxicity to oral mucosa.

In a further embodiment as an oral mucositis preventive, to achieve acceptance of the orally-applied drug in human cancer patients, a low but protective dose of epinephrine, phenylephrine, norepinephrine, or methoxamine, or a combination thereof, is used in order to reduce or minimize any undesirable sensory properties of the orally administered preparation. Such undesirably sensory qualities can include, but are not limited to, a "medicine" taste or bitter taste contributed by the vasoconstrictor molecules. In a preferred embodiment, one or more compounds, for example flavoring agents or additives, are added to the preparation to reduce, mask, or eliminate such undesirable sensory properties and to improve oral acceptance of the preparation by cancer patients.

In another embodiment of the oral mucositis treatment, the method includes a step of treating the oral cavity after the radiotherapy or chemotherapy treatment, with a topical ax adrenergic receptor antagonist (e.g. prazosin) in a moisturizing topical delivery vehicle to minimize or eliminate the dry mouth that can result from the topical vasoconstrictor treatment. In another embodiment, the method is for proctitis prevention, and the rectum is treated with an application of an α adrenergic receptor antagonist in a moisturizing and lubricating foam or suppository to re-establish rectal mucosal secretion and function after the vasoconstrictor treatment.

In another embodiment of this invention, the topical preparation is formulated for use to reduce or prevent oral mucositis, gastrointestinal distress from chemotherapy, or proctitis in patients who develop a mucositis of the interior surface of the rectum after receiving lower abdominal radiation therapy. In these embodiments, the preparation preferably contains a muco-adhesive molecule that enables efficient coating of for example, the mucosa of the oropharynx, gastric or duodenal mucosa, or rectal mucosa with a pharmacologically effective concentration of vasoconstrictor.

According to another aspect of the invention, methods are provided for protecting cells, preferably non-neoplastic cells, from damage during cancer chemotherapy or radiotherapy. The method comprises treating a patient by administering to a population of epithelial cells a preparation as described above, for a time and in an amount effective to protect the non-neoplastic cells from damage during radiotherapy or cancer chemotherapy. The method can also include a step of administering an a adrenergic receptor antagonist to an affected mucosal surface to relieve the vasoconstriction. Preferably such treatment helps to re-establish a moist, functional mucosal surface. In a preferred embodiment, the method is used to prevent alopecia during cancer therapy, by applying the preparation to the scalp. In another embodiment, the method is used to prevent gastrointestinal distress due to cancer therapy by administering the preparation orally. In another embodiment, the method is used to prevent mucositis from chemotherapy or radiotherapy by administering the preparation topically to the appropriate region of the body. In yet another embodiment, the method is used to prevent radiation-induced dermatitis, skin rash, and ulceration at the site of irradiation by applying the preparation to the skin.

These and other features of the present invention will be more fully understood from the detailed description, examples and tables that follow.

Panel B shows a graph of skin blanch response versus time (in hours post first topical application of epinephrine) after a series of topical epinephrine applications to a human arm.

FIG. 7

Panel A: Topical application(s) of vasoconstrictors induces skin blanch in human or rat;

Panel B: Chemotherapeutic agents (e.g. Cytoxan) are systematically cleared from blood over time following intravenous infusion or oral adminsitration. The clearance half-life for Cytoxan is about one hour;

Panel C illustrates that topical application of vasoconstrictors rapidly blanches the skin, consistent with reduced delivery of blood to the treated area. The "**" symbol indicates where the topical vasoconstrictor was applied to skin with a "headstart" of 15-20 min;

Panel D: Results from treatment of 10 day old rat pups with topical 950 mM epinephrine four times in the two hr before administering a single, i.p. dose of Cytoxan (30 µg/gm b.w.);

Panel E is a plot of the skin blanch response for human skin and rat skin (both 10 and 22 day old) as a function of the concentration of vasoconstrictor applied.

Figure 8:
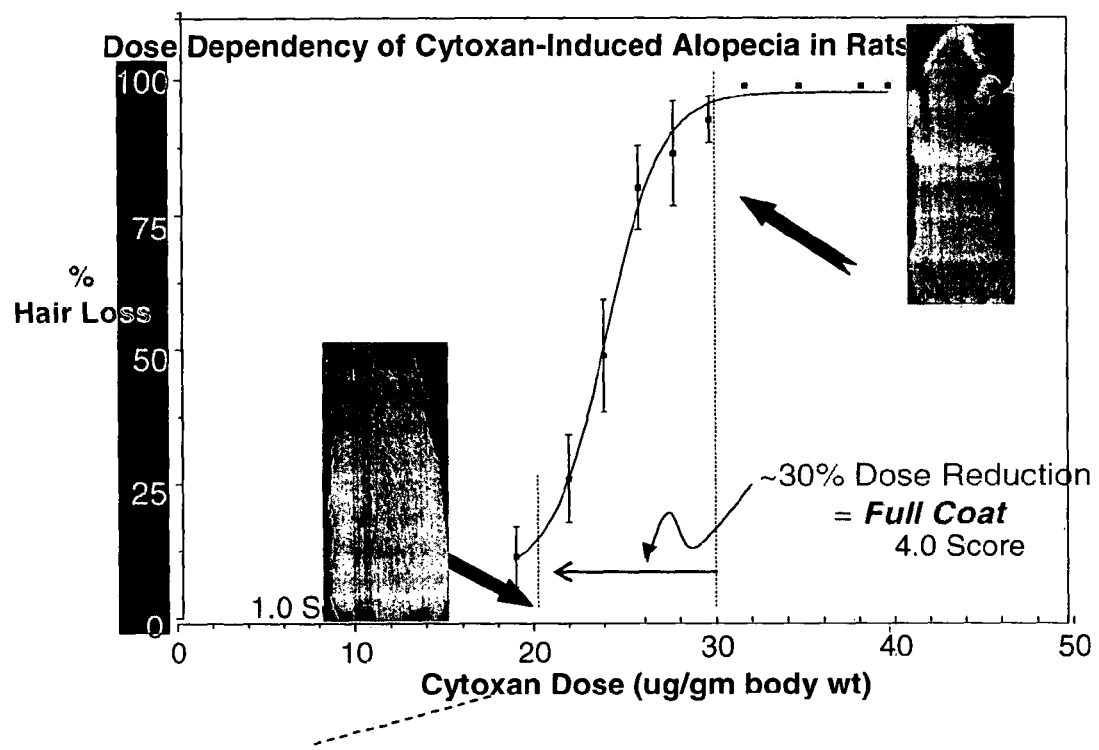

FIG. 8 shows the dose dependency of alopecia induced by Cytoxan in rats. At doses of 20 µg/gm b.w. Cytoxan and lower, treated rats had full coats and retained them into adulthood.

Figure 9:
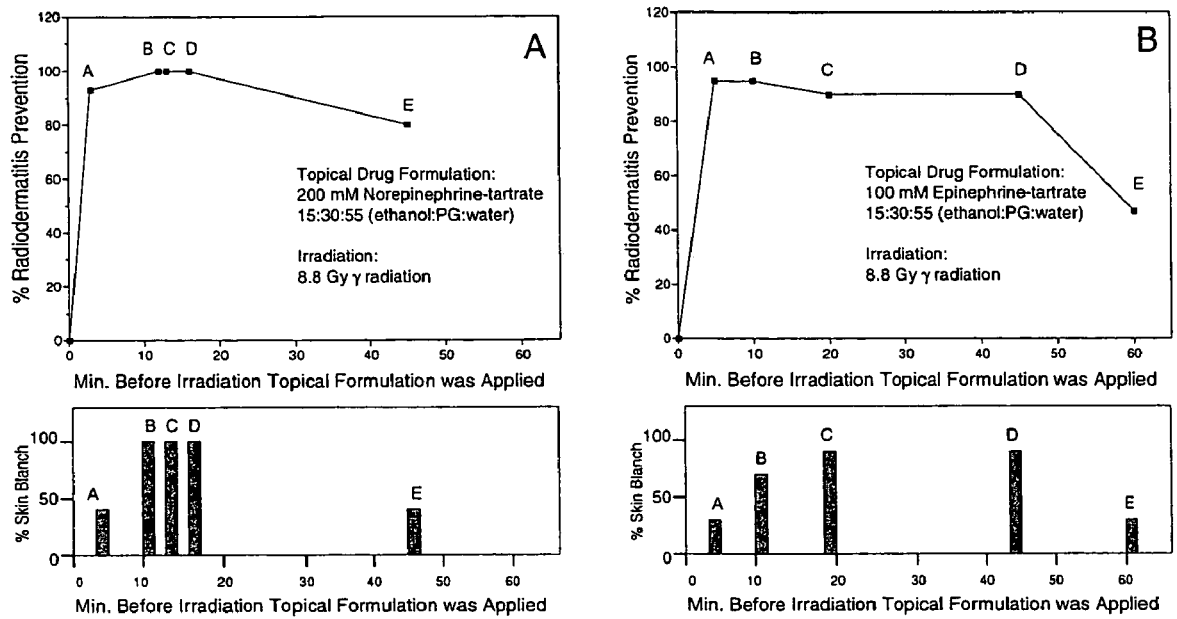

FIG. 9 shows that the pre-irradiation visual skin blanching assessment correlates with the post-irradiation determination of radiodermatitis prevention.

Figure 10:
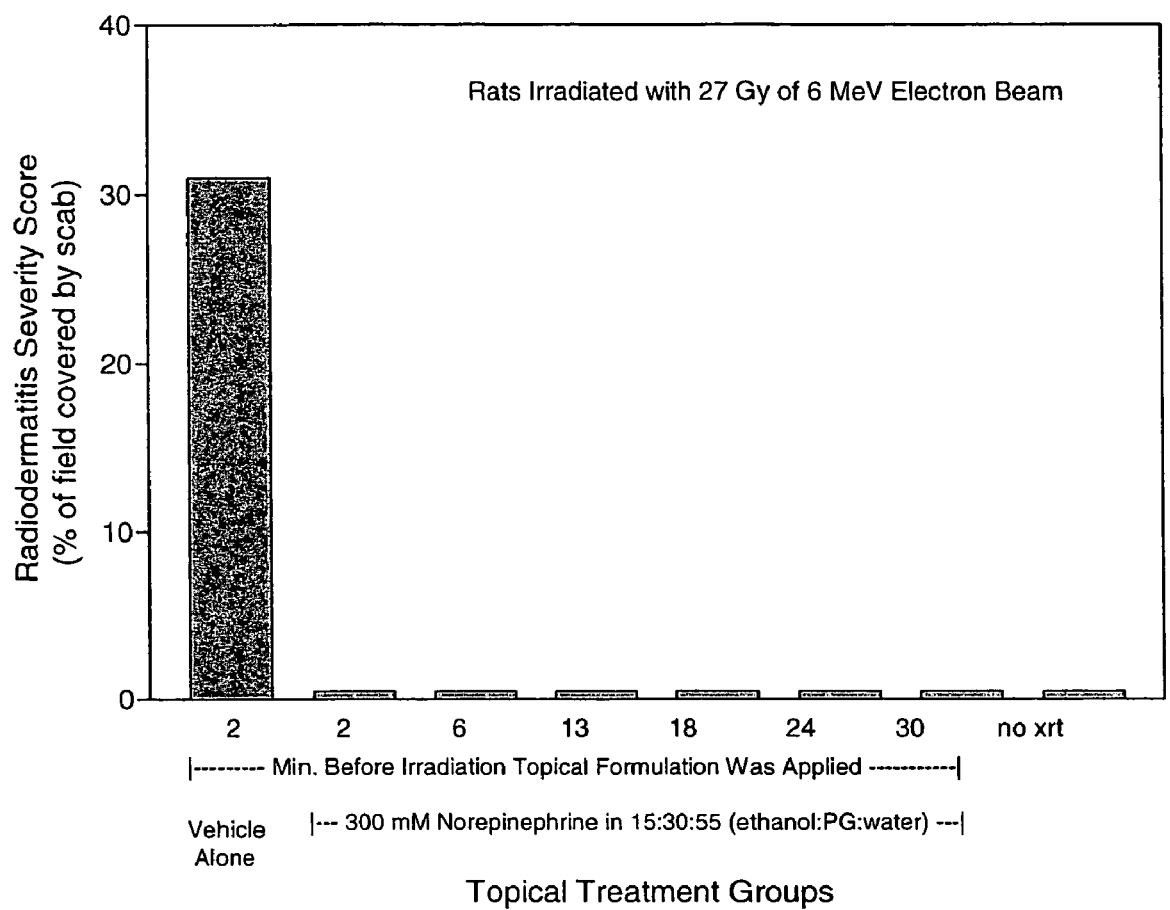

Panel A: treatment with 200 mM Norepinephrine
Panel B: treatment with 100 mM Epinephrine FIG. 10 shows the radiodermatitis severity as a function of the amount time before irradiation that the vasoconstrictor topical treatment was provided.

Figure 11:
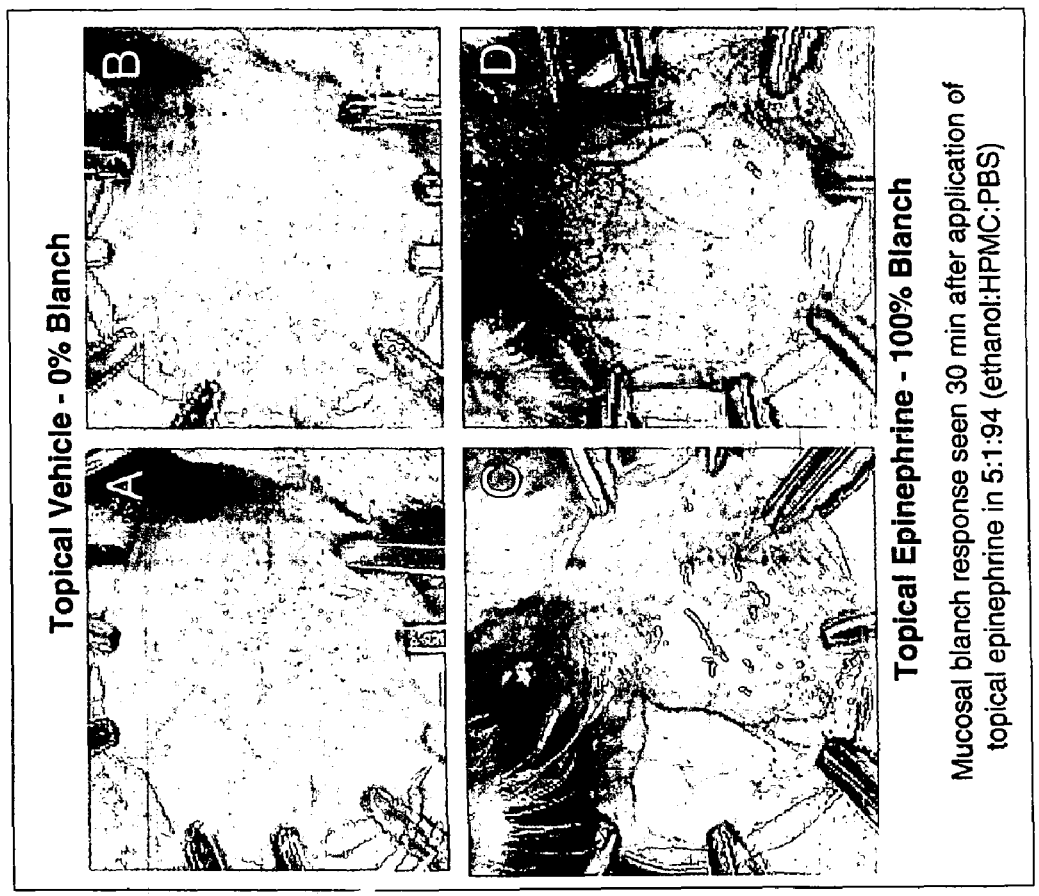

FIG. 11 depicts the blanch response in oral mucosa of Syrian golden hamsters treated topically with vasoconstrictors.

Figure 12:
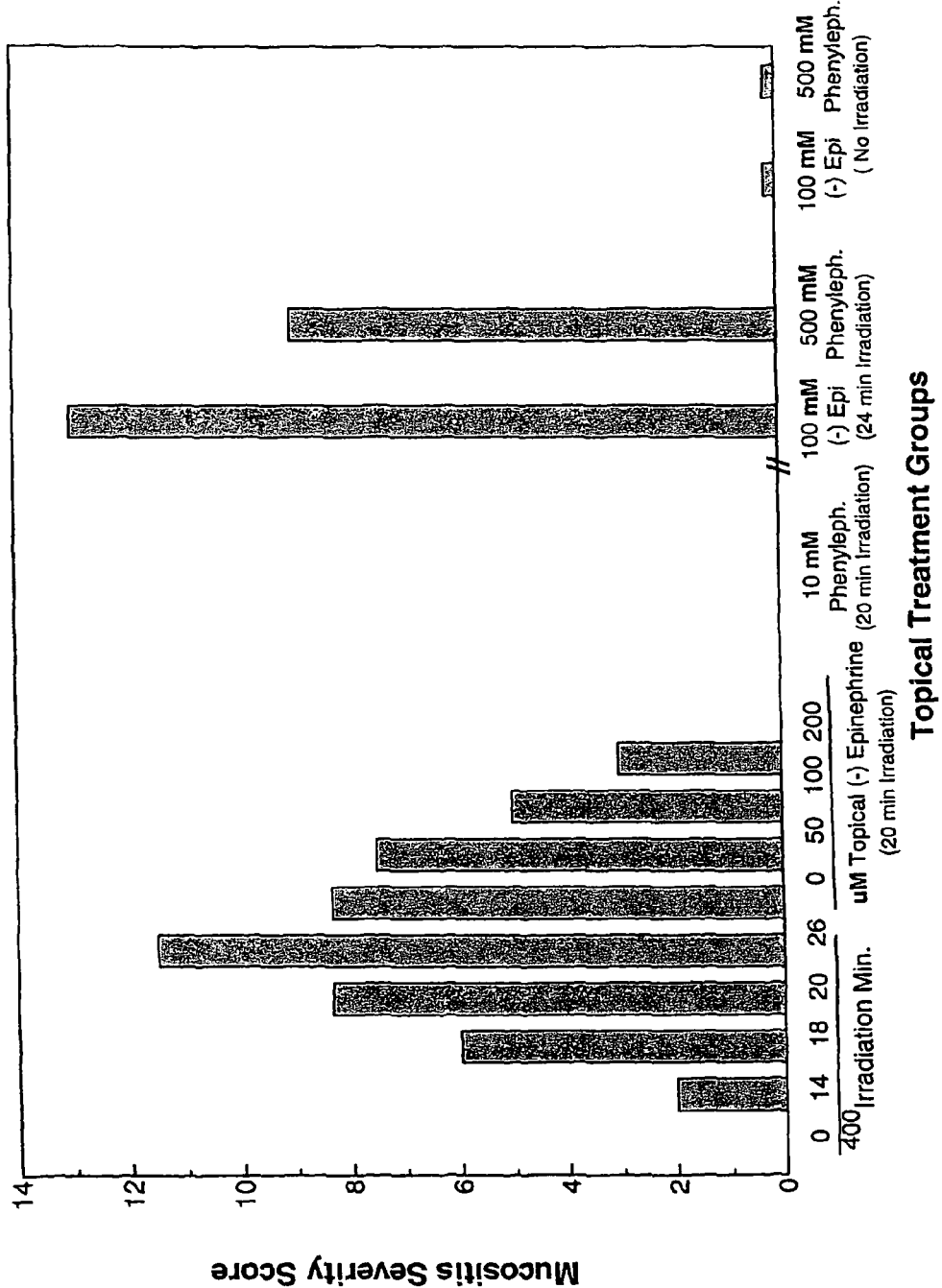

FIG. 12 graphically depicts that increased severity of oral mucositis in the hamster cheek pouch model results from increasing doses of radiation. Topically applied vasoconstrictors at appropriate doses in an appropriate delivery vehicle can prevent the radiation-induced oral mucositis, while high concentrations can when combined with a 40 Gy dose of radiation, cause severe toxicity to oral mucosa.

Figure 13:
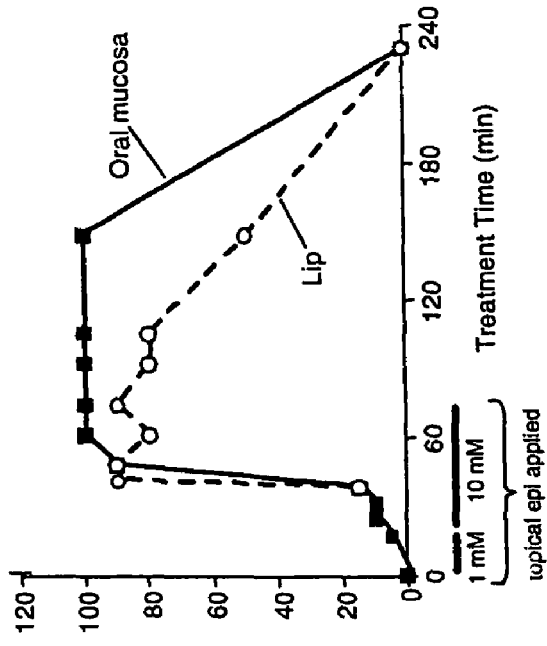

FIG. 13 shows that topically administered (−) epinephrine affects the degree of mucosal blanch observed in human oral mucosa. A plot of maximum blanch response (%) versus time following topical treatment are shown for both oral mucosa and lip.

Figure 14:
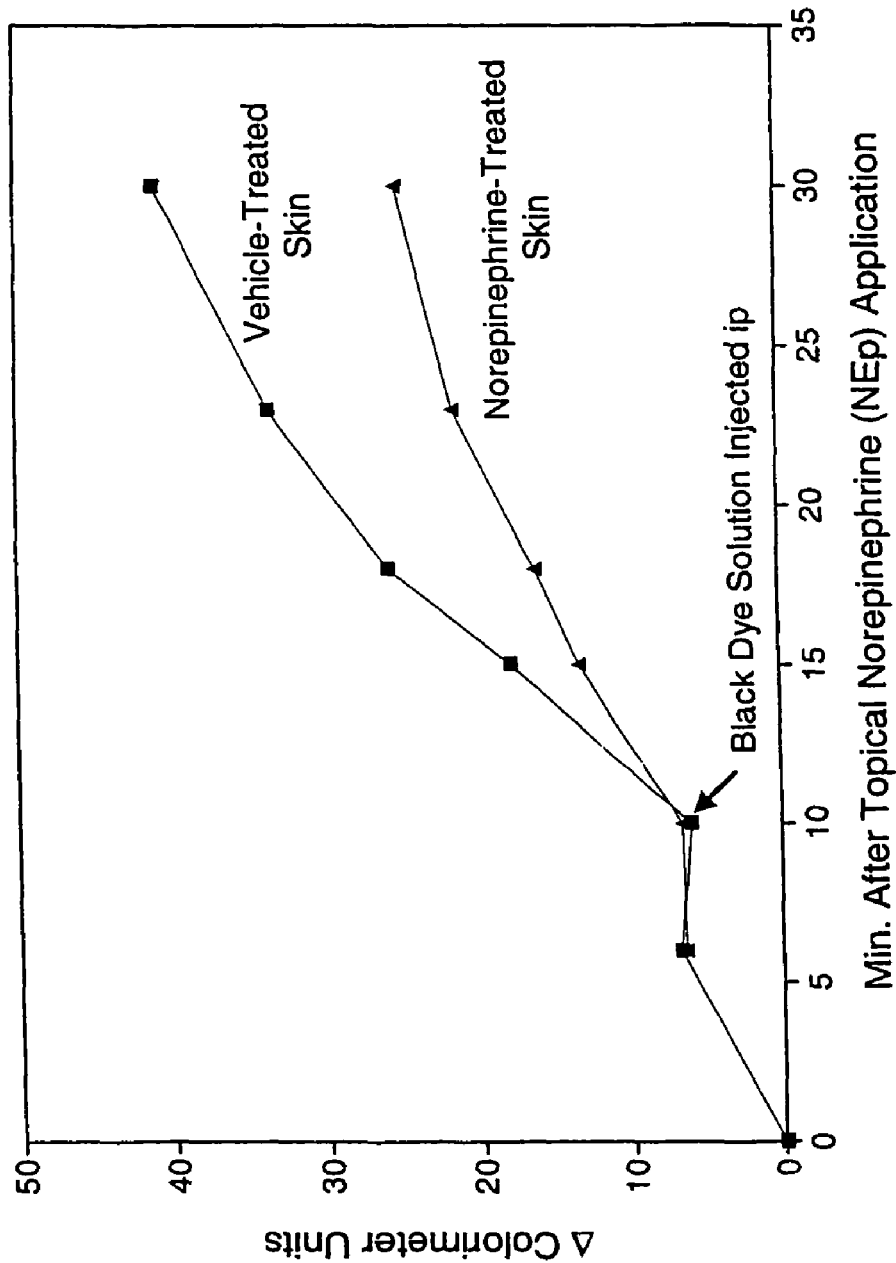

FIG. 14 shows that norepinephrine applied to the clipped backs of rats in an ethanol:PG:water delivery vehicle causes constriction of skin vasculature, and consistent with this, delivery of a systemic, blood-borne dye molecule is significantly reduced to the norepinephrine-treated skin.

DETAILED DESCRIPTION OF THE INVENTION

The present invention provides pharmaceutical preparations and methods for protecting non-cancerous, rapidly dividing cells in a patient's body from the toxic effects of chemotherapeutic agents or radiotherapy administered to the patient. In particular, the preparations and methods of the invention are designed for protecting epithelial cells. Most particularly, the targets are epithelial cells lining hair follicles and epithelial and/or mucosal cells of the skin, mouth, rectum, gastrointestinal and urogenital tract. In one embodiment, the preparations are used to reduce or prevent alopecia during cancer therapy, by topically applying the preparation to the scalp. Another embodiment involves reduction or prevention of gastrointestinal distress due to cancer therapy by administering the preparations orally. Another embodiment involves reducing or preventing mucositis from chemotherapy or radiotherapy by administering the preparations topically to the appropriate region of the body. In yet another embodiment, the preparations are used to prevent radiation-induced dermatitis, skin rash, and ulceration at the site of irradiation by applying them to the skin.

The inventors have identified vasoconstrictor molecules that are effective at preventing unwanted side-effects from chemotherapy and radiation therapy. Vasoconstrictors formulated in delivery vehicles are specifically designed to be administered topically to the skin or surfaces of the mouth or rectum, gastrointestinal or urogenital tract. These topical preparations can protect normal, non-neoplastic cells from damage from cancer therapy. By minimally penetrating a given tissue to which they are topically applied, the vasoconstrictor produces a local protective effect in the intended region. Transient constriction of the local vasculature diminishes delivery of systemic chemotherapy as well as oxygen to the at-risk, non-neoplastic cells that are to be protected. Moreover, topical delivery of a vasoconstrictor should diminish or completely avoid any systemic distribution of the vasoconstrictor, in part because of the self-limiting nature of vasoconstrictor application to skin or mucosa, where the drug itself actively contributes to its self-limiting distribution by constricting the vessels through which it would otherwise be systemically distributed.

Additional aspects of the invention enable the directed manipulation of: i) the concentration of the vasoconstrictor to achieve efficacy but avoid necrotizing toxicity to mucosal surfaces; ii) the penetrance of the topical delivery vehicle through the skin and/or mucosal layer(s) to be treated (for example, in one embodiment by varying the percentages of alcohol, propylene glycol, water in a vehicle), and adhesiveness to mucosal surfaces; iii) the taste of the preparation, so as to enable maximum oral tolerance by human cancer patients. In several of its other aspects, the invention also provides for the topical use of an α adrenergic receptor antagonist to relieve the dry mouth that may occur following the oral use of a vasoconstrictor, and for the avoidance of side-effects that may occur due to vasoconstrictor binding at multiple adrenergic receptor sites (e.g., the α and β adrenergic receptor agonist epinephrine has the potential to induce undesirable cardiovascular side-effects that are not expected to be caused by selective α1 adrenergic receptor-specific agonists phenylephrine and methoxamine).

The undesired cardiac side-effects of systemically-distributed α and β agonists, for example, epinephrine, are well known, although the distant protection of tumor cells by a systemically-distributed vasoconstrictor is possible. Thus, the methods and compositions taught herein provide desired local vasoconstrictor effects in skin or mucosa while avoiding side-effects stemming from systemic administration. The intended protection of normal tissue involves an appropriately chosen vasoconstrictor in combination with an appropriate delivery vehicle, chosen and optimized for a specific administration site (e.g. skin, oral mucosa, rectal mucosa, or the like). Because of the choices of vasoconstrictors and delivery vehicle components that are available, a topically-formulated vasoconstrictor can be used to protect any normal cell type susceptible to the side-effects of cancer therapy that is accessible by topical delivery.

It has been discovered in accordance with the present invention that vasoconstrictor molecules can be efficiently delivered topically to sites of at-risk, non-neoplastic cells where they can bind to adrenergic receptors within the cells of the blood vessel wall, cause constriction of the vasculature, and by so-doing, transiently diminish the delivery of blood-borne chemotherapy drug or oxygen to local, at-risk, non-neoplastic cells. The resultant benefit is greatly reduced apoptosis of local, at-risk normal stem cells and the alleviation of side-effects associated with chemotherapy or radiotherapy. A visual correlate, or surrogate marker, of this process can actually be seen in skin (e.g. human and rat) where topical application of norepinephrine or epinephrine, or generally, a 2-3-fold higher concentration of phenylephrine, causes a visual blanching of the skin. When topically-treated, visually-blanched rat skin is irradiated, dermatitis is completely prevented (Example 2) in the blanched area. This same phenomenon has also been observed in the rodent models for mucositis (Example 4) and alopecia (Example 3).

In comparing, then, the elements found in various embodiments of the invention to the existing art, the following observations can be made. First, the topical application of vasoconstrictors to confer protection against systemically administered, chemotherapy drugs, insofar as is known, heretofore has not been described in the literature. Second, the method of the invention to protect at-risk, non-neoplastic stem cells by the use of topically applied vasoconstrictor is believed to be non-obvious in its various elements. For instance, though Vasin et al. described that a topically applied α adrenoreceptor agonist (phenylephrine) provides radioprotection to mouse skin (Vasin, M., et al., Radiatsionnaia Biologiia, Radioecologiia 44(1):68-71, 2004), they did not teach the design of pharmaceutical preparations that enable vasoconstrictor delivery to the underlying vasculature, while neither killing surface epithelial cells nor enabling systemic biodistribution of the vasoconstrictor. These are important elements of an integrated method to achieve local, topical radioprotection, while avoiding distant, systemic effects. Indeed, the systemic biodistribution of a radioprotective or chemoprotective compound might lead to the unintended effects of protecting the tumor itself from therapy or causing a toxic side effect (e.g., cardiac toxicity as may be induced in humans treated systemically with β2 adrenoreceptor agonists). The current literature provides little or no insight as to how to select a topical delivery vehicle that enables adequate vasoconstrictor delivery to underlying vasculature, while neither killing surface epithelial cells nor enabling systemic distribution of vasoconstrictor. Similarly, the literature provides no insight as to a topical application regimen required to confer protection against protracted exposures to blood-borne chemotherapeutic agents that occur as cytotoxic drugs are metabolized and/or cleared from blood. The literature also does not teach that high doses of epinephrine or phenylephrine can cause necrotizing tissue damage to oral mucosa. In accordance with certain embodiments of the present invention, animal assay systems are provided to establish both efficacy and toxicity and to identify both nontoxic but effective topical doses, as well as toxic, necrotizing doses of epinephrine, norepinephrine, and phenylephrine. In addition, although it has been reported that topical, oral 0.1% epinephrine reduces oral radiation damage in mice, there is no suggestion that flavoring agents are necessary to enable human oral use of vasoconstrictor solutions. Furthermore, there is no teaching that topical, oral delivery of an α adrenergic receptor antagonist after the chemotherapy and radiotherapy threat has passed, enables rapid re-establishment of a moist, lubricated, functioning mucosal surface.

In summary, vasoconstrictors, when specifically formulated for each of the envisioned topical applications, provide an effective means to prevent chemotherapy- and radiation therapy-induced side-effects in cancer patients.

Topical delivery vehicle. Besides a vasoconstrictor at a pharmacologically effective concentration, the preparations of the invention also comprise a topical delivery vehicle. The function of the topical delivery vehicle is to carry the vasoconstrictor to the local vasculature that serves the cell population or tissue targeted for protection from the side-effects of cancer therapy.

The term "topical" denotes the administration of a drug intended to act locally rather than systemically. To inhibit the side-effects of cancer therapy it is important that vasoconstrictors be delivered to the site intended and be restricted from systemic distribution. Restricting vasoconstrictor systemic distribution will have the benefits of avoiding known cardiac side-effects of an epinephrine active agent as well as limiting exposure of distant neoplastic cells to the vasoconstrictor. The local delivery of a vasoconstrictor active agent within the skin or mucous membranes using a noninvasive, topical delivery system has many attractions, including: i) patient acceptability due to the noninvasiveness of the procedure, ii) avoidance of gastrointestinal drug digestion, and iii) avoidance of first-pass liver metabolism of the gastrointestinal-delivered molecule. Numerous components of topical delivery vehicles used in this invention are listed below. Though topical delivery vehicles composed of these elements are known to enable sufficient delivery of small, organic, drug molecules into the skin, topical delivery is also known to be a very inefficient means for delivering the same drugs into the system. As an example, it is estimated that only between 1%-3% of the minoxidil in the topical formulation of 2% minoxidil becomes systemically bioavailable. Also important to aspects of the present invention, vasoconstrictors provide a significant, additional, predisposition to remain local because of their efficient constriction of the vasculature that would otherwise provide their systemic distribution.

Skin delivery systems. Skin delivery systems typically consist of the drug prepared in a solution, emulsion or cream, gel or liposome suspension. The description, composition, production, and applicability of these major types of skin or dermal delivery forms are briefly reviewed as follows.

Figure 1:
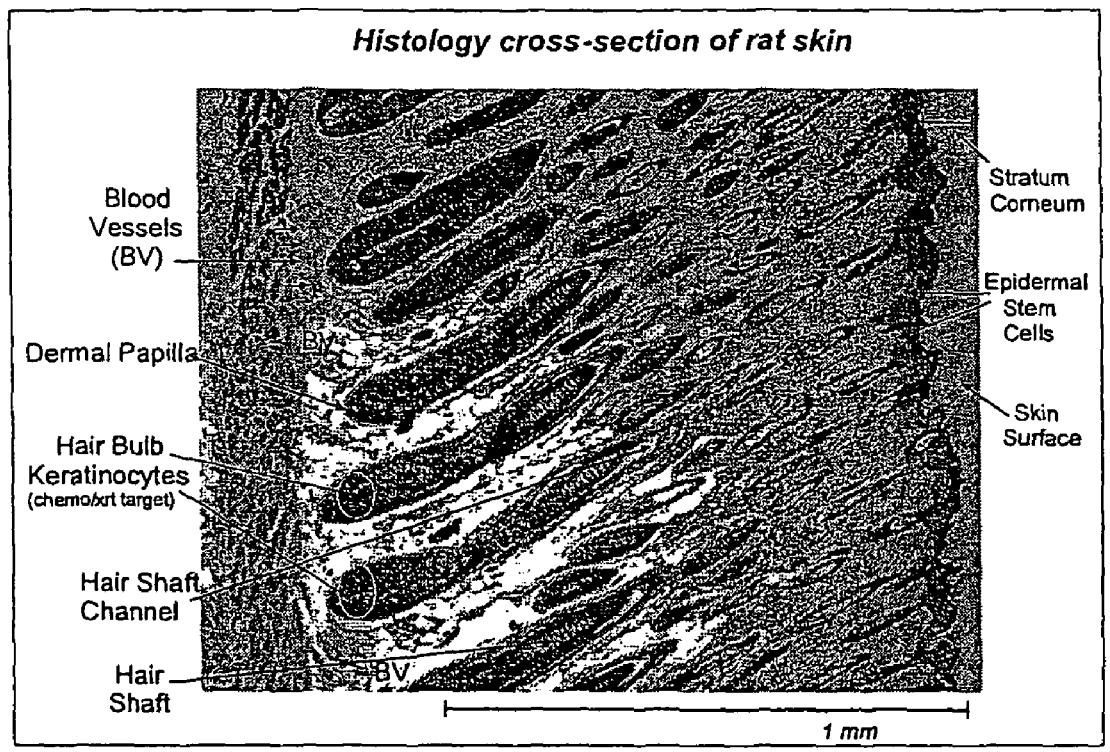
FIG. 1 illustrates a histological cross section of rat skin. It shows the location of the stem cells within the epidermis and hair follicle as well as the dermal vasculature that surrounds the hair follicles and provides blood to the dermis and overlying skin structures.

The skin is a complex multilayer organ with a total thickness of 2-3 mm. Skin consists of two main layers, the dermis and epidermis. The dermis provides physiological support for the epidermis and consists of connective tissue, nerves, blood and lymph vessels, sebaceous and sweat glands. FIG. 1 illustrates the organization of these tissue elements in a cross section of rat skin. Epidermis is about 100 um thick and consists of a number of layers. The stratum germinativum is the basal layer of the epidermis containing the epidermal stem cells. Above the basal layer are the stratum spinosum, the stratum granulosum, the stratum lucidum, and finally the stratum corneum. Each layer is in a different stage of differentiation; during this differentiation the cells migrate from the basal layer to the surface and cornify to form the stratum corneum. The stratum corneum consists of flattened, keratin-filled, former cells. A lipid matrix within the stratum corneum is composed of double-layered lipid membranes composed of cholesterol, free fatty acids and ceramides. The stratum corneum and the lipid matrix layer are primarily responsible for the low penetration rate of most topically delivered substances. This cornified, lipid matrix is the main barrier to percutaneous absorption of molecules, but molecules that loosen or fluidize the lipid matrix of the stratum corneum clearly enhance the permeation of substances through the skin. Some common permeants used for this purpose include alcohols, lecithins, and liposomes.

The skin also contains several other structures within the dermis, including sebaceous (oil) glands, exocrine (sweat glands), and hair follicles. While the majority of the hair follicle is positioned within the dermal layer, the follicle itself is composed of specialized epidermal cells. The follicle consists of an outer basement layer and an outer and inner root sheath that surrounds the hair shaft. At the base of the hair follicle, both the matrix cells and the dermal papilla together produce the hair shaft.

Solutions are the most common formulation for topical drugs, where the active agent is solubilized in a solvent. Solvent-based systems are simple but acceptable topical delivery vehicles. Alcohols are the most commonly used solvents for topical solutions. Typically, the drug is combined into a water and alcohol mixture. The alcohol content varies between 10-100%. Alcohols used include ethanol, propylene glycol, polyethylene glycol, methanol, or butanediol. High alcohol content solutions such as solutions of 70% ethanol in water or those containing, for example, 60% ethanol, 20% propylene glycol and 20% water, are particularly good at penetrating the stratum corneum of the epidermis. Topical minoxil, a hair regrowth treatment, uses the latter formulation as the delivery vehicle.

Solution-based delivery systems are ideal for the delivery of small organic molecules. In a preferred embodiment of the invention, particularly for administration of vasoconstrictor to the stem cells of the epidermis, alcohol-containing solutions are particularly well suited. An aqueous alcohol-based delivery vehicle was proven effective for topical administration of vasoconstrictors (Examples 1, 2, 3, 4). Other advantages of this delivery system include, ease of manufacturing, fast drying on the skin, and ease of analysis of active drug compound after formulation.

Figure 2:
FIG. 2 illustrates how a dye molecule (Nile Red, FW: 318), topically applied to rat skin in an ethanol delivery vehicle, penetrates the epidermis through the stratum corneum and penetrates each of the regularly arrayed hair follicles through the bottom of the follicular bulb.
Figure 2:
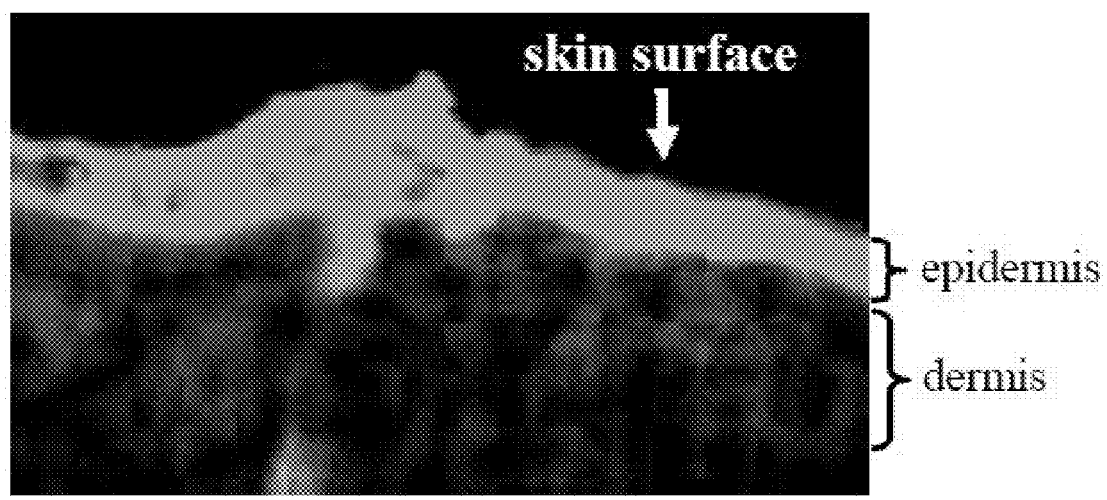

It is preferred for certain embodiments of the invention directed to skin applications, to optimize ethanol, propylene glycol and water percentages to enable sufficient delivery of epinephrine, phenylephrine, norepinephrine, or methoxamine to the skin vasculature, to achieve transient, vasculature constriction, and by so-doing, confer protection to the stem cells of the epidermis and hair follicle. The primary skin vasculature is located within the dermis, largely creating a vascular web surrounding the hair follicle bulbs (shown in FIG. 1). Topical drug delivery to this vasculature is primarily achieved by "transfolicular" delivery, i.e., topically-applied alcohol:water solutions travel within the hair shaft channels to the hair follicle bulb, and then diffuse through the stem cells that comprise the hair follicle bulb to access the dermal vasculature surrounding the bulb. For topical solutions to access dermal vasculature, a minimum percentage of alcohol in the topical delivery vehicle is preferred to enable: i) dissolution or softening of sebaceous oil present in human hair shaft channels, and ii) penetration of the oil-stratum corneum matrix. FIG. 2 shows that a fluorescent dye (Nile Red, FW: 320), when applied to rat skin in an alcohol:water solution, penetrates both the stratum corneum and underlying epidermis as well as it penetrates each of the hair follicle channels, all the way through the base of the follicular bulb.

When a topical vasoconstrictor is applied, as in Example 1, and in related rat skin experiments, there are also functional results (e.g., skin blanching) that indicate that topically applied vasoconstrictor does efficiently access and constrict dermal vasculature. The use of visual assessment, for example of blanching and the like, can provide a "surrogate end point" and allow rapid assessment of a treatment or putative treatment. The use of such a surrogate end point can facilitate development of new or improved topical formulations. As can be seen in the Examples, the desired results, such as reduction or prevention of dermatitis, alopecia, mucositis, and other conditions associated with the side effects of systemic use of chemotherapeutic agents or radiotherapy, will correlate highly with the results from visual observation of blanching or the like.

One aspect of the invention involves optimization of the topical solvent delivery vehicle to enable sufficient delivery of vasoconstrictor to target vasculature while not damaging the overlying epithelial surface. Tables 2-1, 3-1 and 4-1 provide examples of this. In Table 2-1, vasoconstrictors are delivered to dermal vasculature at a sufficient dose to achieve vasoconstriction and radioprotection. The vehicles used range from 55% alcohol (25:30; ethanol:propylene glycol) to 100% alcohol (0:100; ethanol:propylene glycol). In Table 3-1, the 55% alcohol vehicle control showed no toxicity to the skin and no effect upon hair growth. Table 4-1 shows that a topical vehicle for an oral mucosa surface with as little as 10% alcohol (5:5; ethanol:propylene glycol) and physiological saline solution provided sufficient delivery to mucosal stem cells to confer radioprotection while not damaging the mucosa (the Vehicle control showed a score of "0"). An early test of a topical vehicle for skin (containing 50% alcohol) applied to the hamster cheek pouch essentially resulted in "fixation" and dessication of the cheek pouch. Applying the mucosal vehicle of 0.87% phosphate-buffered saline to skin failed because the vehicle "balled up" and ran off the skin.

Gels are semisolids consisting of a gelling agent that is impregnated with liquid solvent. The concentration and the molecular weight of the gelling agent affect the consistency of vehicle formulation. The gelling agent is typically a suspension of either large organic or small inorganic molecules. The large organic molecules, consisting of either natural or synthetic polymers, exist as randomly coiled chains that entangle and form the gel structure. Some common polymers of this kind are natural gums (e.g., xanthan gum) and cellulose derivatives (e.g., hydroxypropylmethylcellulose [HPMC]). The viscosity of gels typically decreases upon application of shear forces, such as vigorous mixing, or upon increases in temperature. A preferred embodiment of this invention for application to mucosal surfaces (e.g., in Example 4) includes formulation of a vasoconstrictor molecule within an aqueous:alcohol gel comprising hydroxypropylmethylcellulose as a gelling agent. The properties of gels are attractive for a topical delivery vehicle because they are relatively easy to prepare and tend to have a long residence time at the site of application allowing the sustained release of an active agent at the desired site.

Liposomes are good vehicles for delivering active components for dermatological applications. Liposomal delivery offers several advantages, including: i) significantly enhanced accumulation of the delivered substance at the site of administration due to high compatibility of liposomes with stratum corneum lipids, ii) ready delivery of a wide variety of hydrophilic and hydrophobic molecules into the skin, iii) protection of the entrapped compound from metabolic degradation; and iv) close resemblance to the natural structure of cell membranes, and with it, similar biocompatibility and biodegradability. Disadvantages of liposome delivery systems include, difficulty of manufacturing and poor long-term stability.

Mucosal delivery systems. Mucosal delivery as defined herein is the local delivery of vasoconstrictors to the mucosa of the mouth, rectum, gastrointestinal, or urogenital tract. The permeability of mucosal surfaces is very high, up to 4000 times greater than that of the skin. This conclusion is clearly supported by the data in Tables 2-1 and 4-1 where discernible radioprotection of a mucosal site (hamster cheek pouch) is seen with as low as 50 μM topical epinephrine, whereas >~20 mM epinephrine applied to skin is required to confer protection against radiation dermatitis. Because of the high permeability of mucosa, caution is also required; a radioprotective epinephrine dose on skin (100 mM, Tables 2-1, 3-1) is highly necrogenic when used for protection of oral mucosa (Table 4-1). Mucosally-active vasoconstrictors can be formulated as solutions, gels or liposome suspensions. The delivery of drugs to the mucosal surface is a very attractive route of administration since the mucosal surface is a common site for the occurrence of unwanted cancer therapy side-effects.

A limitation of mucosal delivery is the lack of vehicle adhesion to the wet mucosal application site. The addition of mucoadhesives to the topical formulation can greatly improve delivery vehicle performance. In another preferred embodiment of the invention for mucosal delivery, the addition of a mucoadhesive molecule to the vasoconstrictor formulation is featured. Example 4 provides two examples of vasoconstrictors, epinephrine and phenylephrine, formulated in a mucosal vehicle containing hydroxypropyl-methylcellulose, that are biologically-active in the treated mucosal epithelium. Mucoadhesive compounds are primarily synthetic or natural polymers that can adhere to the wet mucosal surface, or increase adherence to such surfaces. Mucoadhesive compounds include, for example, synthetic polymers such as, hydroxypropylmethylcellulose, monomeric alpha cyanoacrylate, polyacrylic acid, and poly methacrylate derivatives. Naturally occurring mucoadhesives include as examples chitosan, hyaluronic acid and gums, such as xanthan gum. Many such mucoadhesive compounds are approved for use in pharmaceutical preparations or foods and the use of one or more of these compounds alone or in combination is contemplated herein.

Administration of pharmaceutical preparations containing vasoconstrictors. Depending on the cell population or tissue targeted for protection, the following sites for topical administration of the preparations of the invention are contemplated: oral, nasal, ophthalmic, gastrointestinal, rectal, urogenital and dermal (cutaneous). The pharmaceutical preparations of the invention are conveniently formulated for administration with a biologically compatible medium such as water, buffered saline, ethanol, or polyol (for example, glycerol, propylene glycol). The concentration of a particular composition in the chosen medium will depend on the hydrophobic or hydrophilic nature of the medium, in combination with the specific properties of the delivery vehicle and active agents disposed therein. Solubility limits may be easily determined by one skilled in the art.

Regimens for administration of pharmaceutical preparations. The pharmaceutical preparation comprising the invention may be administered at appropriate intervals, before, during, or after a regimen of chemotherapy and/or radiotherapy, during and after particularly for chemotherapy regimens. The appropriate interval in a particular case would normally depend on the nature of the chemotherapy or radiotherapy and the cell population targeted for protection.

For instance, for prevention of chemotherapy-induced alopecia, solvents, liposomes or other delivery vehicles containing the vasoconstrictor can be formulated to be applied prophylactically to the scalp of a patient prior to scheduled administration of chemotherapy or cranial radiotherapy. By protecting the epithelial cells that line the exposed surface of hair follicles from the chemotherapy drug, the loss of hair commonly associated with cancer chemotherapy can be prevented. Likewise, for the treatment of radiation-induced dermatitis, or oral/gastrointestinal mucositis, the topical preparation can also be applied prophylactically to patients to prevent each of the respective side-effects.

The following Examples are provided to illustrate the invention. They are not intended to limit the invention in any way.

LIST OF TABLES FOR EXAMPLES

Table 1-1. Vasoconstriction of human skin induced by epinephrine or phenylephrine applied topically in an ethanol:propylene glycol:water delivery vehicle.

Table 2-1. Prevention of radiation-induced dermatitis of the skin by prophylactic, topical application of epinephrine, or phenylephrine in an ethanol:propylene glycol:water delivery vehicle.

Table 3-1. Prevention of radiation-induced or Cytoxan-induced alopecia by prophylactic, topical application of epinephrine in an ethanol:propylene glycol:water delivery vehicle.

Table 4-1. Prevention of radiation-induced oral mucositis by prophylactic, topical application of epinephrine or phenylephrine in an ethanol:propylene glycol:hydroxypropylmethylcellulose (HPMC):PBS (phosphate-buffered saline) delivery vehicle.

Table 5-1. Improved taste desire for epinephrine or phenylephrine solutions to which at least one flavoring agent is added.

Table 6-1 The solubility and vasoconstrictive effects (as determined by visual observation of skin blanching) of various topical formulations.

Table 7-1 Properties of three formulations for topical vasoconstrictors on skin blanching of human chest and arm.

Table 8-1 Results for component solubility, skin blanching effect and skin irritation for multiple formulations of topical vasoconstrictors.

Example 1

This example shows that topical application of epinephrine or phenylephrine in an ethanol:propylene glycol:water delivery vehicle confers drug concentration- and time-dependent blanching (vasoconstriction) of human skin. The 0.1% aqueous solution of epinephrine-HCl and the 0.25% aqueous solution of phenylephrine conferred no detectable blanching of the skin over the 180 min observation period of the experiment.

For these experiments, epinephrine-HCl (FW: 220) was dissolved in the indicated 50:25:25 (ethanol:propylene glycol:water) delivery vehicle and phenylephrine-HCl (FW: 204) in the indicated delivery vehicle. Aliquots of a given Topical Vasoconstrictor Formulation (e.g., 10 mM epinephrine) were applied (30 µl at 0 min, 15 µl at 15 min, 30 min and 45 min) to the same 2 sq. cm. skin patch of human skin (on arm), and the Skin Blanch Score was judged at the indicated times. The results are shown in Table 1-1.

TABLE 1-1

| Topical Vasoconstrictor Formulation | Skin Blanch Response* (%) | | | | |
|---|---|---|---|---|---|
| | 0 min | 45 min | 60 min | 150 min | 180 min |
| 0 mM (50:25:35 vehicle) | 0 | 0 | 0 | 0 | — |
| 2 mM epinephrine | — | 10 | 40 | 75 | — |
| 10 mM epinephrine | — | 40 | 60 | 90 | — |
| 50 mM epinephrine | — | 30 | 50 | 85 | — |
| 100 mM epinephrine | — | 85 | 90 | 90 | — |
| 1000 mM epinephrine | — | 85 | 90 | 95 | — |
| 0.1% (4.55 mM) epinephrine (in water) | — | 0 | 0 | 0 | 0 |
| 0 mM (60:30:10 vehicle) | 0 | — | — | — | 0 |
| 30 mM phenylephrine | — | — | — | — | 0 |
| 150 mM phenylephrine | — | — | — | — | 35 |
| 300 mM phenylephrine | — | — | — | — | 50 |
| 1000 mM phenylephrine | — | — | — | — | 60 |
| 2500 mM phenylephrine | — | — | — | — | 70 |
| 0.25% (12.3 mM) phenylephrine (in water) | — | | | | 0 |

*0% = variegated pink skin, 100% = white skin, little variegation

Example 2

This example shows that topical application of epinephrine or phenylephrine in an ethanol:propylene glycol:water delivery vehicle prevents radiation-induced dermatitis of rat skin in a concentration-dependent manner.

For these experiments, epinephrine-HCl (FW: 220) or phenylephrine-HCl (FW: 204) was dissolved in the indicated topical formulation (see Table 2-1). Rats (4-5 week old; backs were previously shaved) received a total of four topical applications to their back at −2 hr, −1 hr, −30 min, and −10 min, and then received 8.7 Gy of γ irradiation over a 4.5 cm² area on their back at 0 min from a $Cs^{137}$ source. The severity of dermatitis was scored 13 days later.

TABLE 2-1

| Cage # | Topical Treatment | Topical Vehicle Formulation* | Radiation Dermatitis Score (% of Irradiated 4.5 cm² Area Free of Scab Material) |
|---|---|---|---|
| 751 | Vehicle | 25:30:45 | 6 |
| 753 | 100 mM epinephrine | 25:30:45 | 100 |
| 754 | 100 mM phenylephrine | 25:30:45 | 45 |
| 756 | 300 mM phenylephrine | 25:30:45 | 95 |
| 715 | 20 mM epinephrine | 50:30:20 | 32 |
| 716 | 1000 mM epinephrine | 50:30:20 | 100 |

*Vehicle is represented as (% ethanol:% propylene glycol:% water)

Example 3

This example shows that topical application of epinephrine in an ethanol:propylene glycol:water delivery vehicle prevents alopecia in a concentration-dependent manner induced by whole-body radiation or Cytoxan.

For these experiments, epinephrine-HCl (FW: 220) was dissolved in the indicated topical formulation (see Table 3-1). Neonate rats (11 days old) received a total of four topical applications to their backs at −2 hr, −1 hr, −30 min, and −10 min, and then received either whole-body radiation (~7.5 Gy [3.65 min] of γ irradiation from $Cs^{137}$ source) or a single intaperitoneal injection of Cytoxan (32 µg/gm b.w.). The severity of the alopecia was scored nine days later—on day 20 of life.

TABLE 3-1

| Cage # | Topical Treatment | Topical Vehicle Formulation* | Alopecia-Inducing Agent | Alopecia Score (% Normal Coat Density in Topical Treatment Area) |
|---|---|---|---|---|
| 751 | Vehicle | 25:30:45 | Irradiation | 0 |
| 757 | Vehicle | 25:30:45 | Cytoxan | 0 |
| 757 | Vehicle | 25:30:45 | None | 100 |
| 756 | 1000 mM epinephrine | 25:30:45 | None | 100 |
| 753 | 1000 mM epinephrine | 25:30:45 | Cytoxan | 40 |
| 647 | 20 mM epinephrine | 50:25:25 | Irradiation | 6 |
| 648 | 100 mM epinephrine | 50:25:25 | Irradiation | 33 |
| 649 | 500 mM epinephrine | 50:25:25 | Irradiation | 45 |
| 650 | 1000 mM epinephrine | 50:25:25 | Irradiation | 94 |
| 564 | 1000 mM epinephrine | 0:100:0 | Irradiation | 95 |

*Vehicle is represented as (% ethanol:% propylene glycol:% water)

Example 4

This example shows that topical application of epinephrine or phenylephrine in a muco-adhesive ethanol:propylene glycol:hydroxypropylmethylcellulose:phosphate-buffered saline delivery vehicle confers concentration-dependent prevention of radiation-induced oral mucositis.

For these experiments, epinephrine-HCL (FW: 220) or phenylephrine-HCl (FW: 204) was dissolved in the indicated topical formulation (see Table 4-1). In an assay based upon Alvarez et al. (Clin. Cancer Res. 9:3454-3461, 2003), Syrian golden hamsters (5-6 weeks old) were anesthetized with Nembutal (60 µg/gm b.w.), their left cheek pouch was everted with a forceps and rinsed (water) and blotted to clean, the cheek pouch was reverted, and ~0.3 ml of the muco-adhesive topical formulation was applied to the inside of the left check pouch using a Q-tip cotton swab (this point represents 0 min). After 12 min, the left check pouch was everted, spread and immobilized with clips across an ~2 cm diameter plastic disc.

Additional topical formulation was applied with Q-tip to uniformly cover the everted, interior surface of the cheek pouch. After 20 min, the vehicle-coated, immobilized cheek pouch was taped into position over a 1.5 cm diameter window bored through a 2.5 cm thick lead plate. The sleeping hamster was immobilized on a small shelf on the plate that enabled cheek pouch irradiation through the window. The lead plate was then positioned between the hamster and the source in a $Cs^{137}$ irradiator, and timed irradiation of the cheek pouch was done.

After irradiation, the cheek pouch was rinsed with water, blotted and reverted. The severity of mucositis in the irradiated cheek pouch was scored 16 days later using the following criteria.

| Scoring Criteria: | Degree of Erythema: | 0 (none)-5 (worst) |
|---|---|---|
| | Degree of Swelling: | 0 (none)-4 (worst) |
| | Degree of Contraction/Rigidity: | 0 (none)-4 (worst) |
| | Pseudomembrane Presence: | 0 (none)-4 (worst) |
| Mucositis Severity Score: | Sum Total = | 0 (none)-17 (worst) |

TABLE 4-1

| Cage # | Topical Treatment | Topical Vehicle Formulation* | Irradiation Time | Mucositis Severity Score |
|---|---|---|---|---|
| | Experiment C | | | |
| 774 | Vehicle | 5:5:3:87 | 0 min | 0 |
| 774 | Vehicle | 5:5:3:87 | 14 min | 3.0 |
| 774 | Vehicle | 5:5:3:87 | 18 min | 6.0 |
| 775 | Vehicle | 5:5:3:87 | 20 min | 8.3 ± 0.3 |
| 775 | Vehicle | 5:5:3:87 | 26 min | 11.5 |
| 775 | 0.00 mM epinephrine | 5:5:3:87 | 20 min | 8.3 ± 0.3 |
| 777 | 0.05 mM epinephrine | 5:5:3:87 | 20 min | 7.5 |
| 778 | 0.10 mM epinephrine | 5:5:3:87 | 20 min | 5.0 |
| 778 | 0.20 mM epinephrine | 5:5:3:87 | 20 min | 3.0 |
| 778 | 0.40 mM epinephrine | 5:5:3:87 | 20 min | 0 |
| | Experiment B | | | |
| 766 | Vehicle | 0:0:3:97 | 24 min** | 8.0 ± 1.7 |
| 765 | 13.5 mM epinephrine + 12.3 mM phenylephrine | 0:5:3:92 | 24 min | 11.7 ± 0.7 |
| 767 | 12.3 mM phenylephrine | 0:5:3:92 | 24 min | 5.0 ± 0.1 |
| | Experiment A | | | |
| 759 | Vehicle | 5:0:1:94 | 24 min** | 8.9 ± 0.1 |
| 760 | 100.00 mM epinephrine | 5:0:1:94 | 24 min | 14.5 ± 2.4 |
| 761 | 500.00 mM phenylephrine | 5:0:1:94 | 24 min | 9.0 |

*Vehicle is represented as (% ethanol:% propylene glycol:% HPMC:% PBS)
0.10% epinephrine-HCl = 4.55 mM
0.25% phenylephrine-HCl = 12.3 mM
**Though exposed for 24 min, due to alignment with $Cs^{137}$ source, these animals received a similar Gy dose as 20 min animals in Experiment C Example 5

This example shows that whereas aqueous solutions of 0.1% epinephrine or 0.25% phenylephrine are scored as having "undesirable" tastes by human subjects, addition of a flavoring agent to mask the taste provides large, significant (2.7-3.1 fold) improvements in the taste descriptors to the "very desirable" range. Such improvements are highly preferred to help maximize human patient compliance for the use of these oral, topical solutions to prevent radiotherapy- or chemotherapy-induced oral mucositis. Flavoring agents for partially or completely masking undesirable tastes are known in the art, and the skilled artisan will appreciate that sweeteners and other flavorings can be used in formulating solutions to increase palatability or acceptability.

For this experiment, taste test solutions were formulated as indicated in Table 5-1. One ml of each solution was placed in a glass vial labeled only by letter. Subjects were asked to taste and record a score for each solution on the Score Sheet shown in Table 5-1. Some subjects indicated that vials M and N "tasted like medicine" or "were bitter."

TABLE 5-1

| Sample | | Desirable Taste Score 0-10<br>0 = Undesirable<br>10 = Very Desirable |
|---|---|---|
| M | | |
| 0.1% | epinephrine | 3.3 ± 0.7 |
| 99% | water | |
| N | | |
| 0.25% | phenylephrine | 2.5 ± 0.5 |
| 99% | water | |
| O | | |
| 0.1% | epinephrine | 8.3 ± 0.5 |
| 0.25% | cherry flavor* | |
| 16% | sucrose | |
| 84% | water | |
| P | | |
| 0.1% | epinephrine | 8.8 ± 0.6 |
| 0.25% | spearmint oil** | |
| 16% | sucrose | |
| 84% | water | |
| Q | | |
| 0.1% | epinephrine | 8.3 ± 0.5 |
| 0.25% | peppermint oil⁺ | |
| 16% | sucrose | |
| 84% | water | |
| R | | |
| 0.25% | phenylephrine | 7.8 ± 0.5 |
| 0.25% | cherry flavor* | |
| 16% | sucrose | |
| 84% | water | |
| S | | |
| 5% | NaCl | 0.5 ± 0.3 |
| 5% | $NaHCO_3$ | |
| 90% | water | |

*S19 Cherry Flavor; LorAnn Oils, Inc., Lansing, MI
**S59 Spearmint Oil; LorAnn Oils, Inc.
⁺S48 Peppermint Oil; LorAnn Oils, Inc.

Example 6

This example relates to comparing different norepinephrine tartrate solutions epinephrine tartrate, and phenylephrine hydrochloride solutions in delivery vehicles comprising different ratios of water, ethanol, and PG.

Aliquots of each vasoconstrictor salt were weighed into glass test tubes. The volume of liquid necessary to achieve the indicated final drug concentration was then added. The percent composition (vol:vol:vol) of each diluent solution (ethanol:propylene glycol (PG):water) is indicated in Table 6-1.

TABLE 6-1

| Diluent Composition ethanol:PG:water vol:vol:vol | Vasoconstrictor concentration (mM) | | Heat required to completely dissolve vasoconstrictor salt (# secs. at 100° C.) | Skin Blanch[1] | Sample status after 24 hr at ~22° C. | Sample status after 24 hr at 4° C. |
|---|---|---|---|---|---|---|
| 12:30:58 | 750  | NEp[2]    | 0  | ++    | clear       | clear       |
| 12:30:58 | 450  | NEp       | 0  | +     | clear       | clear       |
| 12:30:58 | 600  | NEp       | 0  | ++    | clear       | clear       |
| 15:30:55 | 1000 | NEp       | 0  | +++   | clear       | clear       |
| 40:30:30 | 300  | NEp       | 2  | ++    | clear       | clear       |
| 45:25:30 | 300  | NEp       | 2  | ++    | clear       | clear       |
| 15:30:55 | 600  | NEp       | 0  | ++    | clear       | clear       |
| 44:18:33 | 600  | NEp       | 2  | +++   | clear       | clear       |
| 40:25:35 | 600  | NEp       | 2  | +++   | clear       | clear       |
| 45:25:30 | 600  | NEp       | 2  | +++   | clear       | clear       |
| 50:20:30 | 600  | NEp       | 1  | ++++  | clear       | clear       |
| 50:25:25 | 600  | NEp       | 1  | ++++  | clear       | clear       |
| 50:30:20 | 600  | NEp       | 1  | ++++  | clear       | clear       |
| 55:20:25 | 600  | NEp       | 1  | +++++ | precipitate | precipitate |
| 60:20:20 | 600  | NEp       | 2  | +++++ | clear       | clear       |
| 33:33:33 | 1800 | NEp       | 18 | –[7]  | precipitate | precipitate |
| 0:50:50  | 1800 | NEp       | 6  | –     | precipitate | precipitate |
| 0:80:20  | 1800 | NEp       | 24 | –     | precipitate | precipitate |
| 50:30:20 | 750  | Epi (±)[3]| 0  | +++   | clear       | clear       |
| 15:30:55 | 1000 | Epi[4]    | 0  | +++   | clear       | clear       |
| 20:30:50 | 1500 | Epi       | 0  | ++++  | clear       | clear       |
| 60:0:40[6]| 1500 | Epi      | 0  | +     | clear       | clear       |
| 15:30:55 | 2500 | PhE[5]    | 8  | +     | clear       | precipitate |
| 12:30:58 | 3300 | PhE       | 8  | +     | precipitate | precipitate |
| 10:30:60 | 4000 | PhE       | 12 | <+    | precipitate | precipitate |
| 10:30:60 | 5000 | PhE       | 12 | <+    | precipitate | precipitate |
| 10:30:60 | 5500 | PhE       | 16 | <+    | precipitate | precipitate |

[1] Extent of human skin blanch 20 min after topical application (+++++ = 90-100% blanch)
[2] NEp: L (–) norepinephrine-tartrate
[3] Epi (±): (±) epinephrine-HCl
[4] Epi: L (–) epinephrine-tartrate
[5] PhE: R (–) phenylephrine-HCl
[6] 60:0:40: isopropanol:PG:water
[7] Not tested The approximate amount of heat required to dissolve the vasoconstrictor salt in each diluent is indicated. Once diluted, samples were sealed and held at room temperature (~22° C.) for 24 hours and then at 4° C. for 24 hours. Skin blanch induced by the topical formulation was assessed by applying freshly made, clear formulation to human skin shortly after initial mixing. Drug solutions were monitored for the appearance of precipitated material over a 48 hour observation period.

Example 7

This example shows the effects obtained with test solutions containing at least 50% ethanol plus varying ratios of PG and water.

Figure 3:
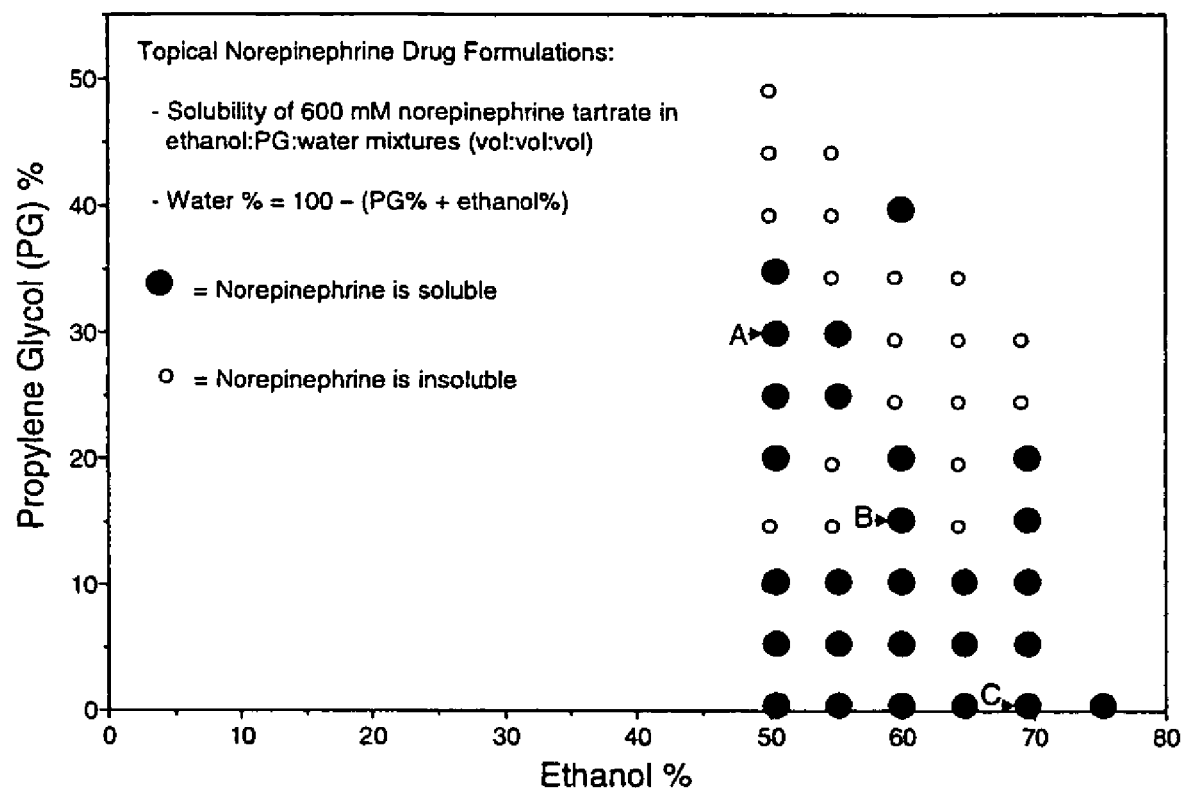
FIG. 3 shows the solubility of norephinephrine in various topical drug formulations comprising mixtures of ethanol, propylene glycol and water. The closed circles represent points wherein the norepinephrine is soluble; the open circles represent points wherein the norepinephrine is not soluble.

L-(–)-norepinephrine tartrate was weighed into glass mini-vials (1.5 ml). Solvent composed of ethanol:propylene glycol (PG):water in the percentages (vol:vol:vol) specified in FIG. 3 was then added to each vial. Vials were heated as necessary to dissolve norepinephrine by touching vials to a boiling water bath for one second increments and then vortexing until clear. Sealed vials were left at room temperature for 24 hours, and at 4° C. for 24 hours. During the two 24 hour incubations, liquid in each vial was examined using a magnifying glass to identify the formation of any crystalline material. If crystals formed, norepinephrine was noted as "insoluble" at that solvent mixture. The data in FIG. 3 show the unpredicted bimodal pattern of norepinephrine solubility. The areas of solubility (e.g., around 50:30:20 and around 60:10:30) are separated by solvent formulations in which norepinephrine was not soluble (e.g., 55:20:25).

Figure 4:
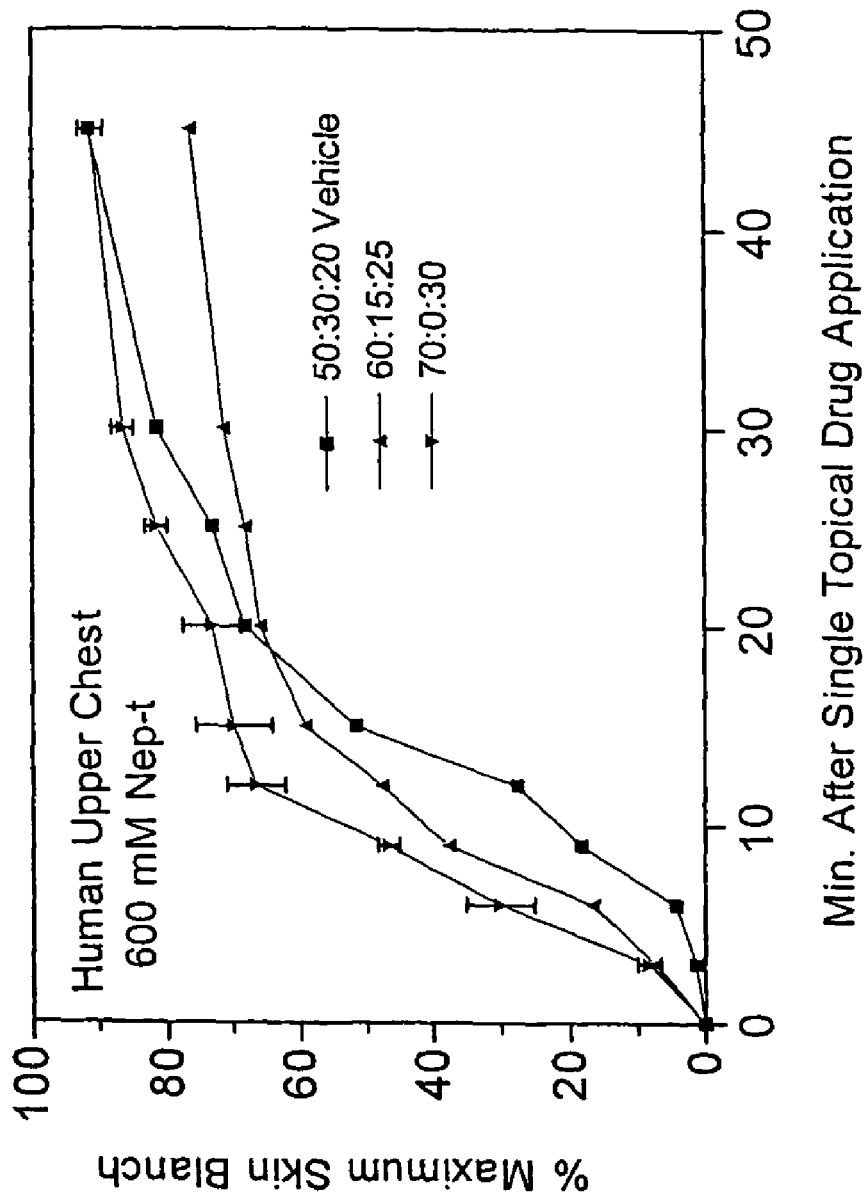
FIG. 4 shows a graph of skin blanching response of the human chest versus time after a single topical application of a drug formulation as indicated.
Figure 5:
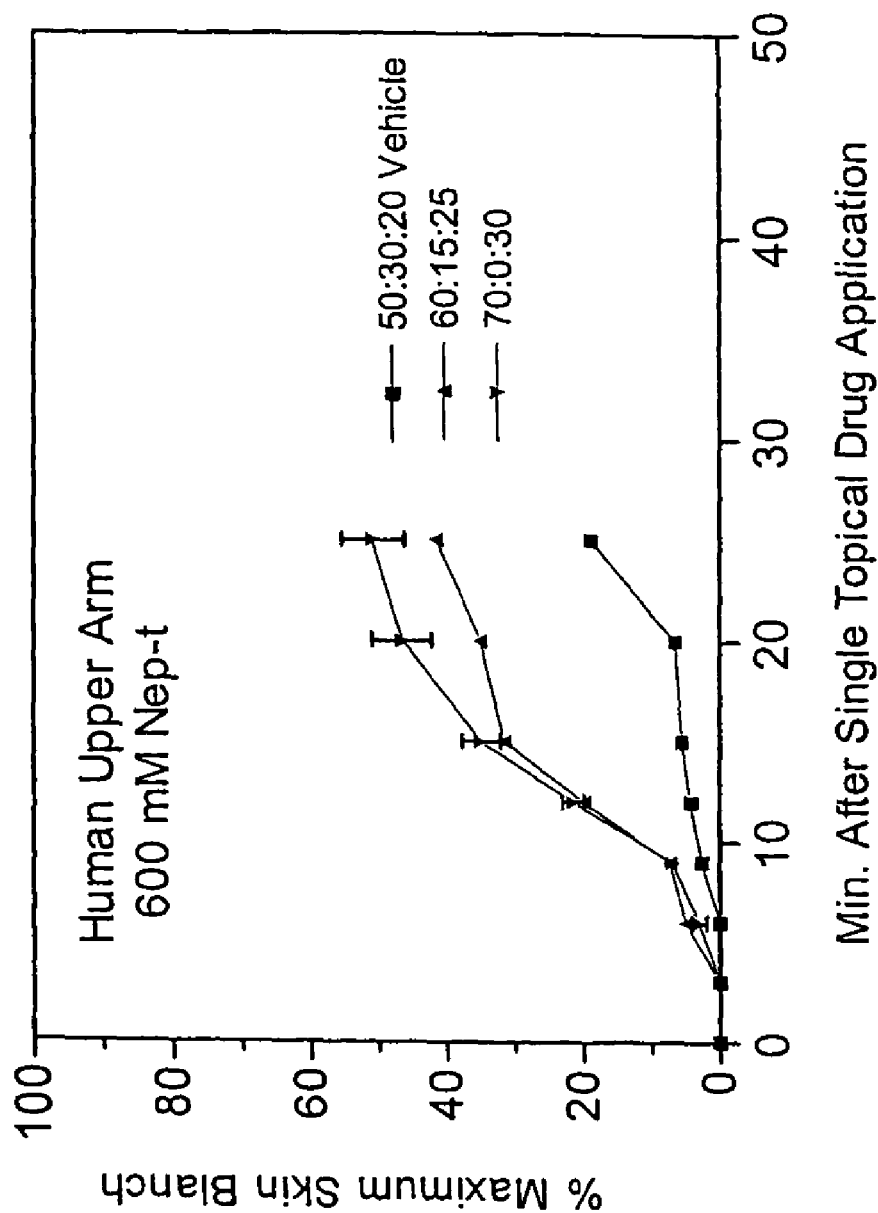
FIG. 5 shows a graph of skin blanching response of the human upper arm versus time after a single topical application of a drug formulation as indicated.
Figure 6:
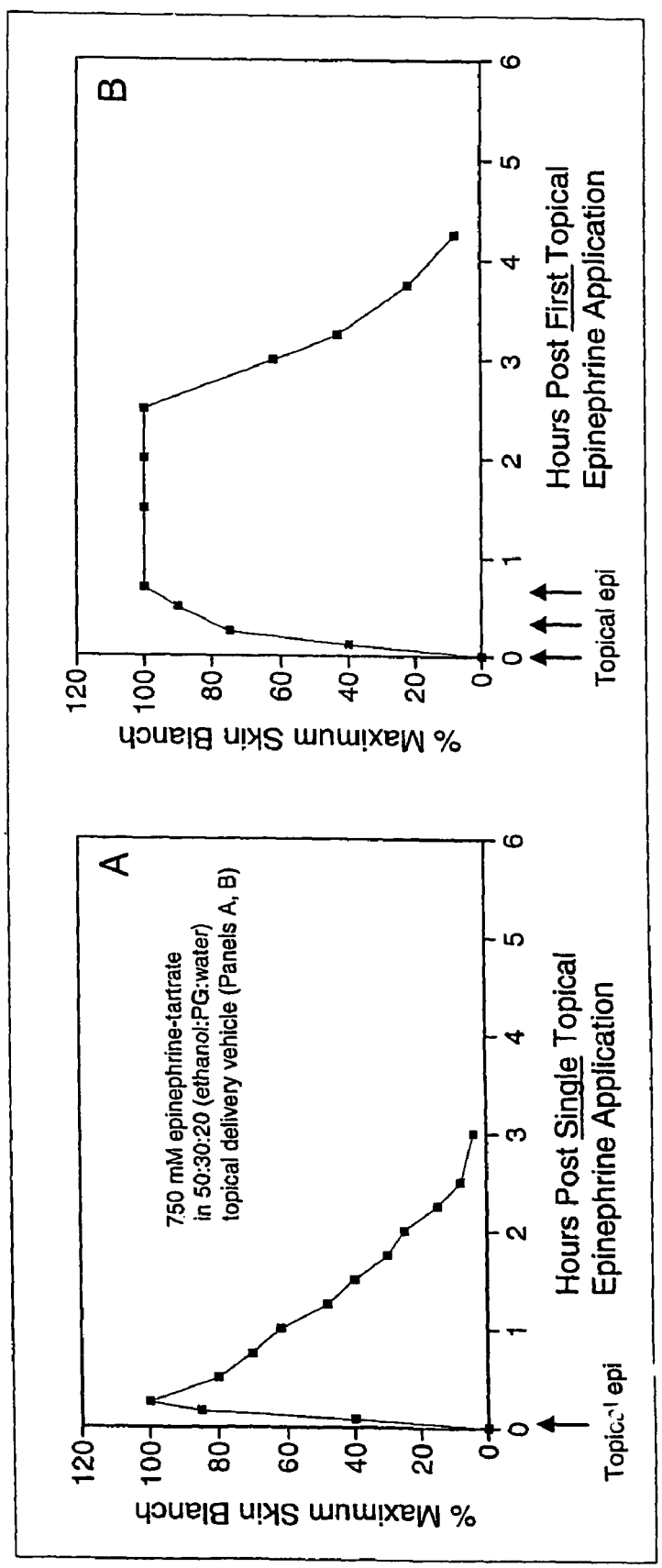
FIG. 6 Panel A shows a graph of skin blanch response versus time (in hours) after a single topical epinephrine application to a human arm.

Three formulations, A, B and C, were chosen for additional characterization (Table 7-1). Triplicate aliquots of each formulation were also applied to human skin on the upper arm and upper chest. For 60 min following topical application, skin blanch at the topical application site was monitored and visually scored (as percentage skin blanch). Skin blanch at 12 min (chest) or 20 min (arm) were recorded. One hour after topical drug application, sites were touched to determine what detectable residue, if any, remained on the skin. Skin blanch was most intense for solutions with higher alcohol content, and the amount of "residue" at the application site directly reflected the propylene glycol content of the formulation. The residue could be detected by a "sticky" quality at the topical site. The results for the chest and arm are shown in FIGS. 4 and 5, respectively.

TABLE 7-1

| Sample | Formulation | Formulation Density (gm/l) | % Skin Blanch[1] | | "Sticky" Residue" at Topical Site |
|---|---|---|---|---|---|
| | | | Chest | Arm | |
| A | 50:30:20 | 0.983 | 28 | 7 | +++++ |
| B | 60:15:25 | 0.961 | 47 | 34 | +++ |
| C | 70:0:30  | 0.931 | 67[2] | 48[3] | 0 |

[1] ~80 μl of formulation was applied with Qtip to ~1 cm² human skin; degree of skin blanch (0-100%) was visually monitored and scored at 12 min (chest) or 20 min (arm) after topical application
[2] p = 0.001 vs. Grp A
[3] p = 0.001 vs. Grp A

Example 8

This example shows the effects that known enhancers of permeation in human skin have upon intradermal delivery of norepinephrine in human skin.

To identify the safest, most efficient means to topically deliver norepinephrine to the dermal vasculature beneath normal, keratinized human skin, L (−) Norepinephrine-tartrate was added to topical delivery formulations composed of water and the indicated permeation enhancers.

In samples where a clear, norepinephrine-containing solution was achieved, an aliquot (~100 μl) was applied to a ~1 $cm^2$ area of human forearm skin using a cotton swab. The extent of skin blanch (i.e., dermal vasculature constriction) beneath the application site was visually scored over the 60 min following application.

The results are provided in Table 8-1 below.

TABLE 8-1

| 300 mM NEp[1] | Liquid Phase | Permeation Enhancers | | | | Components Co-Soluble | Skin Irritation | Skin Blanch[2] |
|---|---|---|---|---|---|---|---|---|
| + | water | | | | | Yes | No | 0 |
| + | water | | | 0.8% SLS[3] | | Yes | No | 0 |
| + | water | ethanol | | 0.8% SLS | | Yes | Slight | + |
| + | water | ethanol | | | | Yes | No | + |
| + | water | ethanol | | | 5% Menthone | Yes | Slight | ++ |
| + | water | ethanol | | | 5% Limonene | No | —[6] | – |
| + | water | ethanol | Transcutol[4] | | | Yes | No | ++++ |
| + | water | ethanol | Transcutol | 0.4% SLS | | Yes | No | ++++ |
| + | water | ethanol | PG[5] | | | Yes | No | ++++ |
| + | water | ethanol | PG | 0.3% SLS | | Yes | No | ++++ |
| + | water | ethanol | PG | | 5% Menthone | Yes | No | +++ |
| + | water | ethanol | PG | 0.2% SLS | 5% Cetyl Alcohol | No | — | – |
| + | water | ethanol | PG | 0.2% SLS | 5% 1-Docosanol | No | — | – |
| + | water | ethanol | PG | 0.3% SLS | 5% Menthone | Yes | Yes | +++++ |
| – | water | ethanol | PG | 0.3% SLS | 5% Menthone | Yes | Yes | – |
| 600 mM NEp | | | | | | | | |
| + | water | ethanol | PG | | | Yes | No | +++++ |
| 750 mM NEp | | | | | | | | |
| + | water | ethanol | PG | | | Yes | No | +++++ |

[1]NEp: L (–) norepinephrine-tartrate
[2]Extent of human skin blanch 20 min after topical application (+++++ = 90-100% blanch)
[3]SLS: sodium lauryl sulfate
[4]Transcutol: diethylene glycol monoethyl ether
[5]PG: propylene glycol
[6]—: Not tested Example 9

This example shows that a single topical application of epinephrine or norepinephrine in a topical delivery vehicle can rapidly induce human skin blanch, including on human scalp, and that multiple topical applications can provide a sustained skin blanch response that could correlate with sustained protection against systemic chemotherapy over 2-3 hr.

750 mM solutions of L-(–)-epinephrine tartrate or L-(–)-norepinephrine tartrate were prepared by dissolving crystalline vasoconstrictor salt in 50:30:20 mixtures of ethanol:PG:water and applied topically to human skin on either the arm (FIG. 6, panels A, B) or scalp. Digital images were recorded at the specified times after topical application to record the extent of skin blanch and to demonstrate that the skin blanch is restricted to the site where the topical drug was applied. An aliquot (40 μl) of drug formulation was applied to ~1 $cm^2$ of skin to yield a topical dose of ~30 $\mu mol/cm^2$. At both the arm and scalp application sites, partial skin blanch was visible by 10 min and complete skin blanch was generally visible by 15 min after topical drug application (panels A and B). The norepinephrine application site on the scalp included both hairless forehead and hair-covered scalp, and the rapid onset and dissipation of the blanch response was the same in these contiguous areas, with no discernible toxicity to skin or hair.

A "skin blanch" area (in human or rat) is characterized at its peak (100%) as a white skin patch with a sharply demarcated edge. This blanch spontaneously dissipates with time to become skin with the color of the surrounding skin with no demarcated edge.

A single, topical drug application (see, for example, FIG. 6, panel A) enables rapid skin blanch and relatively quick blanch dissipation. A single application schedule is expected to be useful in the treatment of cancer radiotherapy patients who are irradiated 2-3 min/day five days per week.

Multiple, topical drug applications (FIG. 6, panel B) enable a more sustained skin blanch. The slower dissipation of vasoconstriction observed for multiple drug applications is expected to be useful for the treatment of cancer chemotherapy patients who receive intravenous chemotherapy over a 1-2 hour period once every 3-4 weeks.

Example 10

This example shows that topical application of epinephrine in an appropriate delivery vehicle to 10 day old rat pups induces an area of skin blanch at the application site, alone, and that this same area retains full, normal coat growth after animals are treated with whole body γ radiation.

A 950 mM solution of (±) epinephrine HCl (epi) in 50:30:20 ethanol:PG:water, or the vehicle alone, were applied to the backs of 10 day old neonate rats (40 μl, 25 ul, 25 μl, 25 μl at –120, –60, –30 and –10 mins, respectively) before the animals received 7.5 Gy whole-body γ radiation from a $Cs^{137}$ source. At specific time points, digital images were recorded to show areas of skin blanch in the epi-treated rats. Skin blanch was not seen in rats treated with vehicle alone. At 30 min and 60 min into the 120 min topical epi application, white areas of skin were visible within the epinephrine-treated skin field that generally over-lapped and merged into a single blanched field by 120 min. A comparison of areas where the coats of 20 day-old rats were retained following topical epi treatment and irradiation on day 10, indicated that in those animals where discrete areas of skin blanch were seen prior to irradiation, discrete areas of protected coat were seen in the 20 day old animals. For most rats treated with topical epinephrine on day 10 of life and then irradiated, the confluent area of skin blanch covering the epinephrine-treated skin was associated with a confluent area of protected coat on day 20. Animals treated with only topical vehicle before irradiation showed no detectable skin blanch prior to irradiation and were completely denuded when scored on day 20. The areas of protected coat of the rats on day 20 were retained and integrated into the animals' mature coat that re-grew after the whole-body radiation.

Example 11

This example illustrates prevention of chemotherapy-induced alopecia in an animal model in accordance with one embodiment of the invention.

Figure 7:
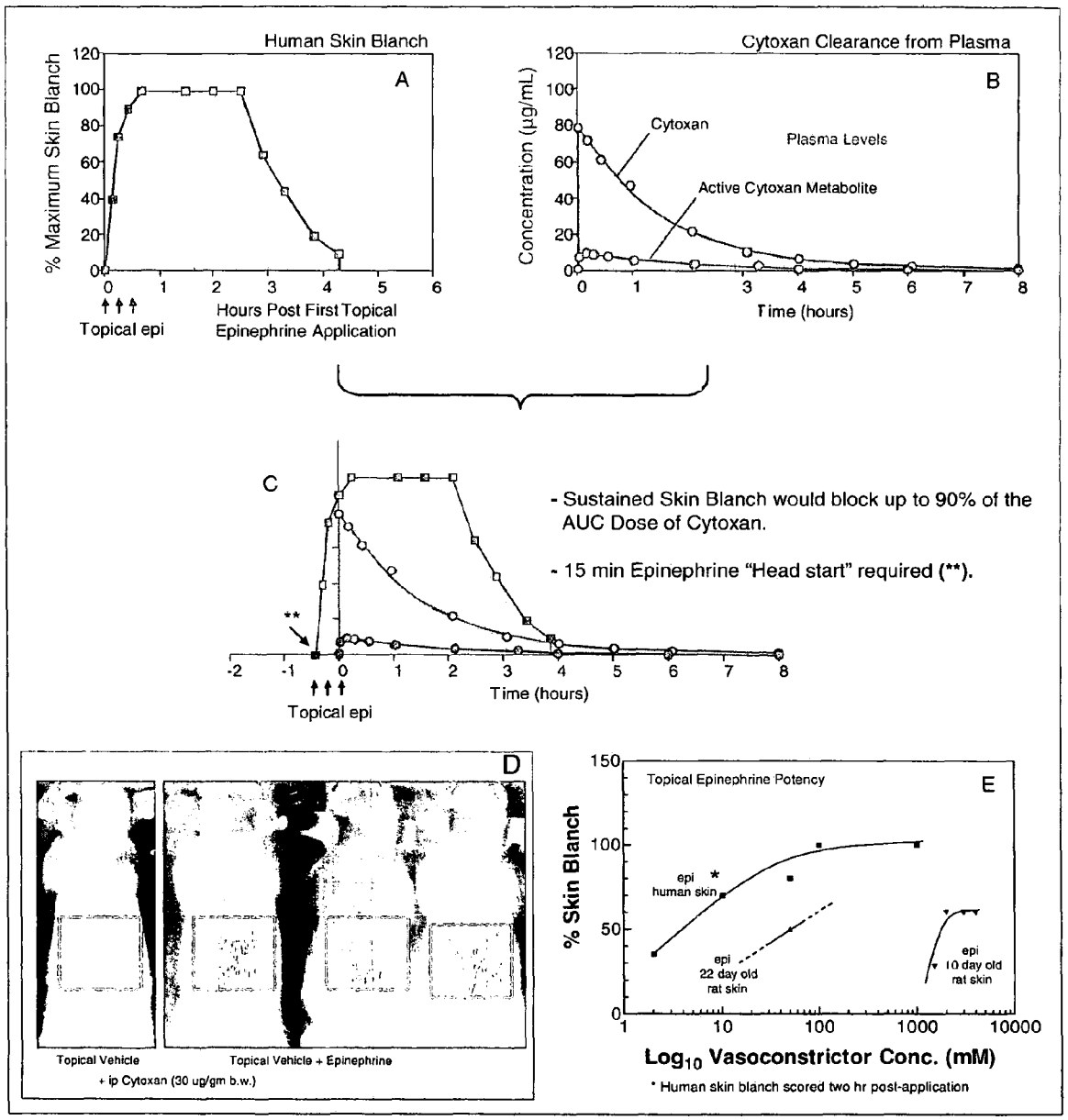

Topical applications of a vasoconstrictor such as norepinephrine or epinephrine induce skin blanch in human or rat skin (see e.g., FIG. 7, panel A). Multiple applications can induce skin blanch lasting for 2-3 hr or more before spontaneously dissipating. When constricted, blood flow to dermal vasculature and its dependent stem cells in epidermis, hair follicle, and the like, is greatly reduced.

Following intravenous infusion of chemotherapy, such as for Cytoxan, as shown in panel B of FIG. 7, the drug(s) is systematically cleared from blood plasma over time. The clearance half-life for Cytoxan is about one hr (panel B).

Panel C illustrates that when topical vasoconstrictor, such as epinephrine, is applied to skin, the skin rapidly blanches. The skin blanch response is consistent with reduced delivery of blood to the skin. If the topical vasoconstrictor is applied to skin, such as the scalp, with a "headstart" of 15-20 min (see ** notation in FIG. 7, panel C), blood delivery to skin and its stem cells will be reduced while systemic blood levels of chemotherapies such as Cytoxan are at their highest levels (e.g., 0-2 hr).

In an accompanying Example, we show that as little as a 30% reduction in Cytoxan dose results in virtually complete retention of the rat's coat, and that as little as a 20% reduction in Cytoxan dose could enable retention of "cosmetically acceptable" scalp hair in human cancer patients.

For panel D, 10 day old rat pups were treated with topical 950 mM epinephrine four times in the two hr before they received a single, intraperitoneal dose of Cytoxan (30 µg/gm b.w.). Areas treated with topical epinephrine contained protected coat on day 20 whereas areas treated with topical vehicle alone contained no protected coat. The partial coat protection seen in epinephrine-treated, 10-day-old rats is consistent with the reduced response to vasoconstrictors (and the modest skin blanch, which is maintained relatively briefly) that is seen in the skin of 10 day old rats compared to older rats (or to humans) (panel E).

Example 12

This example helps to define the percentage reduction in blood flow to hair follicle-containing skin in order to prevent Cytoxan-induced alopecia.

Ten-day old Sprague-Dawley rats (four animals per treatment group) were given intraperitoneal injections of Cytoxan (cyclophosphamide; Sigma # C0768) dissolved in water at the indicated doses. On day 20 of life, coat density on the dorsal back of each animal was visually scored as a percentage of the normal coat density for an untreated 20 day old rat. The results are shown in FIG. 8. At 30 µg/gm b.w. Cytoxan and higher doses, the rats were nude on day 20; at 20 µg/gm b.w. Cytoxan and lower doses, the rats had full coats that were stably retained into adulthood.

Davis, S. T. et al. (Science 291:134-137, 2001) indicate that up to 50% of hair density can be lost due to cancer chemotherapy and still be judged as cosmetically acceptable by cancer patients. This observation, in light of the data in FIG. 8, implies that a 20-30% reduction in the blood-borne dose of Cytoxan that is delivered to hair follicle stem cells would yield a cosmetically acceptable hair density following chemotherapy.

Example 13

This example shows that induction of skin blanch in norepinephrine- or epinephrine-treated rat skin is accompanied by protection against the Grade 2-4 dermatitis that normally follows γ irradiation of the skin.

Adult rats (40-45 gm) were clipped to remove the coat covering their dorsal backs. Aliquots (100 µl) of topical drug formulation containing 200 mM norepinephrine or 100 mM epinephrine were applied once to the backs of the rats, and at set time points afterward, a rectangle (1.5 cm×3 cm) within the topical treatment field received an 8.8 Gy dose of γ radiation from a $Cs^{137}$ source. Just prior to irradiation, the degree of skin blanch within the topical treatment field was also visually scored (0-100% blanch). Animals were anesthetized with 30 µg/gm b.w. sodium pentobarbital prior to irradiation. Following irradiation, rats were returned to cages, and 13 days later the severity of radiodermatitis within the irradiated rectangular field was visually scored and photographed. The results are shown in FIG. 9. A "Radiodermatitis Severity Score" between 0 and 100 represents the percentage of the irradiated field that is covered by scab material on day 13 following irradiation. With an 8.8 Gy dose of γ radiation, vehicle treated animals have a grade 3-grade 4 dermatitis (i.e., 100% scab) covering the irradiated rectangle. The "% Radiodermatitis Prevention" score (shown in FIG. 9) equals [100–Radiodermatitis Severity Score].

Single, topical applications of norepinephrine or epinephrine in ethanol:PG:water delivery vehicles were very effective in producing "radioprotection windows" that spanned from the earliest time-point tested (3 min) to at least 45 min. There was a strong, positive correlation between the extent of skin blanch at the start of irradiation and degree of radioprotection. The 8.8 Gy γ radiation dose (1.72 Gy/min) took 5.1 min to administer, so for the earliest time points (e.g., 3 min) significant, additional blanch likely occurred during the irradiation itself.

Example 14

This example shows that induction of skin blanch in norepinephrine-treated rat skin is accompanied by complete protection against the Grade 2 dermatitis that normally follows 6 MeV electron beam irradiation of the skin.

Adult rats (40-45 gm) were clipped to remove the coat covering their dorsal backs. Aliquots (100 µl) of topical drug formulation containing 300 mM norepinephrine were applied once to the backs of the rats, and at set time points afterward, a rectangle (1.5 cm×3 cm) within the topical treatment field received a 27 Gy dose of 6 MeV electrons from a linear accelerator. Animals were anesthetized with 30 µg/gm b.w. sodium pentobarbital prior to irradiation. Following irradiation, rats were returned to cages, and 13 days later the severity of radiodermatitis within the irradiated rectangular field was visually scored and photographed. A "Radiodermatitis Severity Score" between 0 and 100 represents the percentage of the irradiated field that is covered by scab material on day 13 following irradiation.

The results are shown in FIG. 10. Single, topical application of norepinephrine in an ethanol:PG:water delivery vehicle was very effective in producing a "radioprotection window" that spanned from the earliest time-point tested (2 min) to 30 min. The 27 Gy 6 MeV electron dose took several mins. to administer, so for the earliest time point (2 min) significant, additional blanch likely occurred during the irradiation itself.

Example 15

This example shows that topical application of epinephrine in an appropriate delivery vehicle can induce a rapid and complete blanch of oral mucosa.

To determine whether topical application of a vasoconstrictor could induce a blanch response in oral mucosa, formulations containing epinephrine or phenylephrine were applied topically to the cheek pouch oral mucosa of Syrian Golden hamsters. Use of the hamster cheek pouch for studies of chemotherapy- or radiotherapy-induced mucositis has been previously reported (Alvarez, E., et al. Clin. Cancer Res., 9: 3454-3461, 2003). Hamsters were anesthetized with sodium pentobarbital, the cheek pouch was everted with forceps, rinsed with water and blotted, and immobilized on a 2 cm diameter inert plastic disk using stainless steel clips (see panels in FIG. 11). A topical formulation containing 10 mM epinephrine-HCl or 10 mM phenylephrine-HCl in a 5:1:94 (ethanol:hydroxypropylmethylcellulose:phosphate-buffered saline [PBS]) topical delivery vehicle, or the delivery vehicle alone, was applied to the surface of the cheek pouches. Digital images were recorded.

After 30 min of topical treatment, cheek pouches with vehicle alone looked no different than they did prior to treatment (see FIG. 11, panels A and B). Cheek pouches treated with topical epinephrine or phenylephrine became white and translucent with none of the tissue "pinkness" seen in untreated or vehicle-treated controls (FIG. 11, panels C and D). In other treatment groups, the degree of blanch at 30 min was dependent upon the concentration of epinephrine or phenylephrine used in the topical formulation. Similar blanch responses were observed when topical epinephrine or phenylephrine formulations were dispensed into cleaned cheek pouches that had been re-positioned within the sleeping hamster's cheek and then everted and photographed after 30 min.

Example 16

This example shows that increasing doses of γ radiation cause increasing severity of oral mucositis in this hamster model, that increasing doses of epinephrine applied topically in an appropriate delivery vehicle can completely prevent this radiation-induced oral mucositis, that applying a dose (10 mM solution) of the α1 adrenergic receptor specific agonist, phenylephrine, to the cheek pouch can completely prevent radiation-induced oral mucositis, and that very high doses of topical epinephrine or phenylephrine, when combined with a 40 Gy dose of γ radiation, cause severe toxicity to oral mucosa, which is completely absent without the accompanying 40 Gy γ radiation.

A published hamster model (Alvarez, E., et al., Clin Cancer Res. 9:3454-3461, 2003) was used to determine whether topical application of a vasoconstrictor in an appropriate delivery vehicle could prevent oral mucosa breakdown and mucositis following mucosal irradiation or systemic chemotherapy.

In a standard experiment, the left cheek pouch of the anesthetized animal is everted with a forceps, washed free of its contents, blotted, and then reverted or re-positioned to its original site within the hamster's cheek. The cheek pouch has a capacity to hold 200-300 μl of liquid before any spills into the hamster's mouth. Thus, a drug can be "topically" applied to the inner mucosal surface of the cheek pouch by simply pipetting liquid into the cheek-pouch "vessel." Filling the cheek pouch, waiting briefly, and then emptying it before irradiation is analogous to the human "swish and spit" application protocol. For most of the experiments, rather than using a simple liquid formulation, a liquid containing a gelling agent such as 1-3% hydroxypropylmethylcellulose (HPMC) was used. This loose gel at room temperature, containing the vasoconstrictor of interest, is applied to the inside of the cheek pouch using a cotton swab (QTip). At the animal's body temperature, it becomes a soft, flowing, mucoadhesive solution that effectively coats the entire surface to which it is applied.

Typically, after a 5-20 min treatment, the topically "filled" cheek pouch is carefully everted with a forceps, its contents blotted, and the cheek pouch is then spread and immobilized with clips across an inert, plastic disk (2 cm diameter, see FIG. 13, panel B). The exposed "inner" surface of the immobilized cheek pouch is then coated again, using a cotton swab, with the topical drug formulation. The immobilized cheek pouch and hamster are then carefully positioned on a lead plate (2.5 cm thick) so that the cheek pouch is resting over a small window that is directly in line with the $Cs^{137}$ source when the plate is placed inside of the $Cs^{137}$ γ irradiator. Other lead plates are used to form a small enclosure in which the animal sleeps while irradiation of the cheek pouch, only, occurs.

Using a mucoadhesive topical delivery vehicle helps to keep the surface of the cheek pouch wet and drug-coated during the 20-min irradiation, particularly as the surface of the immobilized cheek pouch rests vertically when being irradiated.

Mucositis of increasing severity was observed with exposure times of 14-30 min; a 24-min exposure roughly equals the 40 Gy exposure used by Alvarez et al. (2003). At the end of the irradiation, the cheek pouch is rinsed with water, blotted, and repositioned to its normal site within the hamster's cheek. The anesthetized animals awaken, and 16 days later (Alvarez et al., 2003) the animals are again anesthetized, and the cheek pouch is everted and photographed.

"Mucositis Severity Scores" are assigned on day 16 following irradiation. The aggregate score incorporates subscores for erythema (0-5), edema (0-4), tissue rigidity (0-4) and pseudomembrane formation (0-4). Mucositis Severity Scores in the 11-13 range are similar in severity to a human Grade 3 mucositis. At an 11-13 score diffuse patches of pseudomembranous ulcers are visible, as well as severe erythema and edema; the pouches also become more rigid and are less amenable to spreading over the plastic disks.

FIG. 12 shows several important results: i) Mucositis Severity Scores increase as the dose of γ radiation increases; ii) topical application of increasing doses of (−) epinephrine to the mucosal surface protects against γ radiation-induced pathology, with 400 μM being completely protective; iii) topical application of 10 mM phenylephrine, an α1 adrenergic receptor-specific agonist with no cardiac-associated side effects, to the mucosal surface is completely protective; iv) the combination of large excess doses of (−) epinephrine or phenylephrine with 24 min of irradiation (~40 Gy) induces severe mucosal pathology; and v) large excess doses of (−) epinephrine or phenylephrine without irradiation induce no discernible mucosal pathology.

Topically applied phenylephrine (10 mM), an α1 adrenergic receptor-specific agonist with no cardiac-associated side-effects, was also effective in completely preventing the γ radiation-induced mucositis.

Example 17

This example shows that epinephrine applied to human oral mucosa in an appropriate topical delivery vehicle can induce a sustained mucosal blanch that would be expected to provide protection against both systemic chemotherapy and external beam irradiation.

In the experiment, (−) epinephrine-tartrate was dissolved in an ethanol:phosphate-buffered saline:hydroxypropylmethylcellulose:flavoring:sucrose vehicle and then diluted with vehicle to either 1 mM or 10 mM concentration. An early application of epinephrine to the tongue showed that it had a mild "medicine-like" taste so that a cherry flavor (LorAnn Oils, Inc) and an aliquot of a concentrated sucrose solution were added to the delivery vehicle. A QTip wetted with the 1 mM solution was used to swab the lower lip and oral mucosa adjoining the lower lip during the first 20 min. Seeing little blanch response, a QTip wetted with the 10 mM solution was then used to swab the lower lip and oral mucosa four times over the next 50 min. The results are shown in FIG. 13. Images were taken and then scored for the degree of mucosal blanch observed. Within 20 min of initiating topical 10 mM (−) epinephrine treatment, clear blanching of the lip and mucosa were seen, and as shown, this lasted for 1½-2 hr before spontaneously dissipating to yield normal color lip and mucosa by 3 hr.

These results provide a proof of principle that vasoconstrictor can be topically applied to human oral mucosa and that sustained blanch is possible for periods long enough to exclude delivery of chemotherapy-laden blood to mucosal structures while the chemotherapy is progressively cleared from the circulating blood plasma compartment.

Example 18

Determination of the % blood flow reduction to provide 100% protection from radiodermatitis or radioinduced alopecia.

This example shows that norepinephrine applied to the clipped backs of rats in an ethanol:PG:water delivery vehicle causes constriction of dermal vasculature. Consistent with this, skin delivery of a systemic, blood-borne dye molecule is significantly reduced in the norepinephrine treated rat skin. The norepinephrine concentration (300 mM) and delivery vehicle composition used (50:30:20) were identical with those used in parallel experiments where they were shown to confer complete protection against, for example, external beam radiation (gamma or electron beam).

Exclusion of Systemic Dye from Skin Following Topical Application of Norepinephrine:

400 μl of a black dye solution was injected into each test rat as an ip bolus at 10 min after topical treatment with either 300 mM norepinephrine or vehicle alone. Colorimeter measurements of skin color in patches were made and the progression was recorded from 0 through 30 min. The change in colorimeter units between the 0 min reading and readings at indicated time points are plotted in FIG. 15. Colorimeter measurements of skin color were made using a CR-400 colorimeter (Minolta Corp.).

Colorimeter readings indicate that delivery of systemic, blood-borne dye molecule is reduced by 39% to norepinephrine-treated skin at the 30 min time point. The same results were obtained with two additional treated rats. It was observed that the onset and duration of the dye exclusion phenotype (FIG. 14) is the same as the radiodermatitis "protection window" that is conferred in rats treated at 0 min with topical 300 mM norepinephrine in an ethanol:PG:water delivery vehicle.

Example 19

Exemplary Formulation of Vasoconstrictor plus Vehicle for Delivery to Intradermal Vasculature in Keratinized Skin and Scalp Many applications described herein preferably provide for the delivery of a vasoconstrictor to the intradermal vasculature that lies about 1 mm beneath the stratum corneum surface of keratinized skin and scalp in humans and other mammals. FIG. 1 shows the small blood vessels that form a meshwork around the "hair bulb keratinocytes" at the base of the hair follicle; these cells are the primary target for apoptosis in mammals exposed to radiation or systemic chemotherapy.

The dermal blood vessels provide nutrients to the hair follicle cells at the dermal papilla where blood vessels intimately associate with hair bulb keratinocytes.

Preferential delivery of a topically applied vasoconstrictor to the dermal vasculature requires:

i) uniform spreading of the drug-containing solution over the skin target area, for example, the scalp surface if preventing alopecia, or the upper chest and axilla if preventing radiodermatitis in a radiotherapy patient, ii) penetration of the oily stratum corneum to allow diffusion directly into the dermis as well as diffusion through the oily sebum that is extruded into the hair follicle channel by sebaceous glands.

In "transfollicular" delivery, the delivery vehicle preferably allow softening and/or dissolution of the sebum and diffusion of the drug-containing vehicle to the hair bulb, and diffusion through and around the hair bulb cells to reach the vasculature within the dermal papilla.

Application of an aqueous epinephrine solution directly to human skin results in the solution "beading up" and rolling off the skin. Example 1 shows that consistent with this, there is no detectable blanching of the treated skin. FIG. 2 shows that when the fluorescent dye, Nile Red, (MW: 320; for comparison, norepinephrine-tartrate FW: 337) is dissolved in an ethanol vehicle and then applied topically to rat skin, at 30 min, both the epidermis and the overlying stratum corneum are loaded with dye molecule. Each of the regularly spaced hair follicles is also stained, and is equally stained, irrespective of the follicle diameter, which indicates that the dye is equally distributed throughout all aspects of the hair follicle structure. In both the left and right panels of FIG. 2, the fluorescence background within the dermis is significantly higher than it is outside of the tissue section, suggesting the dye has also diffused at a lower concentration throughout the dermal connective tissue.

Initial work here with topical delivery of epinephrine, phenylephrine and norepinephrine was guided in part by the work of Tata et al. (Relative Influence of Ethanol and Propylene Glycol Cosolvents on Deposition of Minoxidil into the Skin. J. Pharm. Sci., 83: 1508-1510, 1994), who demonstrated transcutaneous delivery of minoxidil by variations in a two-part ethanol:PG topical delivery vehicle. Because norepinephrine and related catecholamines are either primary or secondary amines, it was herein discovered that a third, aqueous component was required for a topical delivery vehicle that enabled dissolution of the catecholamines, particularly at the concentrations found to provide drug efficacy in unbroken rat or human skin. Although current pharmaceutical formulations containing these catecholamines exist, in each case, the formulations (both drug concentration and delivery vehicles) were neither functional for the practicing the methods taught herein, nor useful nor instructive as to how to achieve efficacy when applied topically to human skin.

Thus, the need for useful formulations of topical vasoconstrictor for application to squamous (keratinized) skin in human cancer patients to prevent either alopecia or radiation dermatitis led us to identify several criteria that were applied in developing preferred formulations, these criteria included:

i) rapid absorption of the topical drug formulation, preferably with no undesired residue on skin;

ii) rapid onset of skin blanch following topical drug application;

iii) a topically applied drug solution with a pH roughly equivalent to that of normal skin;

iv) solvent characteristics that enable dissolution of high concentrations of catecholamine, preferably without substantial precipitation of the active agent during protracted storage, either at room temperature or at refrigerator temperature;

v) desired wettability properties, for example, a formulation density (or viscosity) low enough to spontaneously wet a sponge applicator used to apply drug solution to skin or scalp;

vi) a vasoconstrictor that is a potent α1 adrenergic receptor agonist to enable constriction of peripheral vasculature, but is not a β2 adrenergic receptor agonist to avoid any possible cardiac tachycardia/arrhythmia side effects associated with β2 agonists As disclosed herein, each of the above requirements has been successfully addressed.

i) The experiments described in Example 7 and FIG. 3 involved the preparation and analysis of 600 mM solutions of norepinephrine-tartrate in 46 formulations, where percentages of the three solvents (ethanol, PG and water) were systematically varied. Sustained solubility of the norepinephrine as well as pharmacologic performance of three of the 46 formulations were scored. Of the three formulations studied in detail, A (50:30:20; ethanol:PG:water; vol:vol:vol), B (60:15:25), and C (70:0:30), both A and B left an undesired "sticky" residue at the topical treatment site that was detected 1 hr after drug application. Formulation C, composed of 70% ethanol and 30% water, was completely absorbed, with no detectable residue, within minutes of application.

Norepinephrine is a potent, pharmacologically-active agent, and is listed as a toxin for purposes of regulation. Radiotherapy patients undergo treatment for example, five times per week for six weeks. For reasons of safety, as well as simple convenience for patients, topically applied drug should be rapidly absorbed to enable the daily return of clothing to the treated skin site (e.g., shoulder and axilla of breast cancer patients) without drug residue on skin, or for example without undue safety risks—such as an accumulation on clothing that small children could contact when being held.

ii) Example 7 and FIGS. 4 and 5 describe the response time for a skin blanch response occurring in the chest and upper arm skin of human volunteers. For human radiotherapy patients, scheduling of irradiations is tightly controlled because of the great expense of the linear accelerators and the large number of patients who have to be processed on specific days without the option of re-scheduling. As such, a given patient may be in the clinic for 15-20 min per visit, and the irradiation (e.g., 2 Gy/day) may take only 1-3 min of this time. A topically-applied vasoconstrictor formulation needs to initiate the skin blanch response quickly so that the patient can be irradiated with the expectation of radioprotection, while not causing impractical delays in the radiation facility. Examples 13 and 14 using rat models of irradiation, showed that the blanch window adequately predicted the radioprotection window. Moreover, as can be seen in Example 13, radioprotection slightly preceded the blanch response within the limits of scoring. Formulation C in Example 7, which has 600 mM norepinephrine in a 70:0:30 vehicle, induced the blanch response quickly, even in the upper arm site. The upper arm appears to be heavily keratinized and relatively slow compared to other arm, chest or neck sites that have been tested.

iii) The normal pH of skin falls between 4 and 5.5, and greater alkalinity of skin is associated with greater capacity to support growth of skin pathogens such as *P. acnes*. The unadjusted pH of a 600 mM solution of norepinephrine-tartrate dissolved in a 70% ethanol:30% water vehicle formnulation (e.g. Fomnulation C) is 4.1. The pKa's of both ionizable protons on tartaric acid result in a mildly acidic water-ethanol solution that is highly compatible with skin application with no discernible irritation after multiple applications.

iv) Preferably, pharmaceutical formulations are designed so that each element of the formulation remains soluble for the storage life of the product. The data in Example 7 and FIG. 3 show that sustained solubility of 600 mM norepinephrine-tartrate in the three-part ethanol:PG:water vehicle is not completely intuitive. An "island" of solubility is found around the 50:30:20 formulation. Norepinephrine-tartrate was found, somewhat unpredictably, to be stably soluble in ethanol:water alone solutions. Formulation C (70:0:30) provided a stable solution of a concentration of norepinephrine-tartrate (600 mM) that had acceptable activity for inducing the desired blanch response. Phenylephrine-HCl, an α1 adrenergic receptor-specific agonist, is not preferred as a vasoconstrictor for topical application to keratinized skin because, as shown in Example 6, it is not stably soluble in topical vehicles at the concentrations required to induce an acceptable blanch response.

v) Wettability is a useful property for topical formulations of the type described herein. The density (0.931 gm/liter) of the Formulation C 70:0:30 norepineprine-tartrate solution is significantly less than that of water. When 50 μl aliquots of Formulation C were delivered to the surface of commercially available sponge applicators, the liquid spontaneously wetted the sponge. In cancer patients, it will be important that the topical norepinephrine formulation be applied to desired sites, such as scalp and eyebrows to prevent alopecia, without for example drainage into eyes, or the like. Thus, a sponge applicator that can be used to apply a thin film of liquid on target sites will be very useful. Some of these sponge applicators are filled by gravity where liquid from a ruptured storage vial flows to the top of a sponge and the bottom of the sponge is then used to apply the solution to skin. It is thus very useful and highly preferred that the drug formulation can spontaneously wet an applicator, for example, a sponge, to enable drug application to scalp or other keratinized skin.

vi) To induce constriction of dermal vasculature, the topically applied vasoconstrictor molecule for use herein is preferably an agonist of the α1 adrenergic receptor found on plasma membranes of smooth muscle cells within the dermal vessel walls. But, a highly preferred second requirement, in order to improve the drug's risk profile, speed regulatory approval, and garner physician product acceptance, is that the molecule not be an agonist of the β2 adrenergic receptor. β2 adrenergic receptors mediate the tachycardia and/or arrhythmia effects that are commonly associated with the systemic or intra-cardiac injection of epinephrine.

Phenylephrine and methoxamine are perhaps logical choices, but as seen for phenylephrine in Example 6 (and separately for methoxamine), it lacks the potency to adequately induce skin blanch when applied to unbroken human skin. It should be noted, that because oral and other mucosal surfaces are approximately 4000-fold more absorbent than unbroken skin, phenylephrine remains an excellent choice as an active agent to induce mucosal blanch and confer the mucosal radioprotection and chemoprotection that is associated with the blanch phenotype.

As can be seen from Table 19-1 below, an acceptable solution for a vasoconstrictor to apply to keratinized skin is norepinephrine. Its binding affinity (potency) for the $\alpha 1$ adrenergic receptor is slightly better than for epinephrine, and it is not an agonist of the $\beta 2$ receptor, so it can't confer the tachycardia/arrhythmia effects.

TABLE 19-1

| Drug | Adrenergic Receptor Specificity* |
|---|---|
| Epinephrine | $\alpha_1, \beta_1, \alpha_2, \beta_2$ |
| Norepinephrine | $\alpha_1, \beta_1, \alpha_2$ |
| Phenylephrine | $\alpha_1$ |
| Methoxamine | $\alpha_1$ |

*Roth, Lefkowitz, Caron, Structure and function of the adrenergic receptor family. Adv. Exp. Med. Biol. 308: 223, 1991.

Norepinephrine is an $\beta 1$ adrenergic receptor agonist, and as such, at pharmacologic concentrations in blood it could increase blood pressure. Without limiting the invention to any particular mode of operation, it is believed that as a vasoconstrictor, norepinephrine applied topically to skin and delivered by diffusion to dermal vasculature, is self-limiting in its distribution. In addition to the self-limiting nature of topical norepinephrine application, there are also two very efficient enzymes, COMT (catechol O-methyl transferase) and MAO (monoamine oxidase) widely distributed in both tissues, blood and blood cells that catabolize catecholamines including norepinephrine. Thus, the Formulation C provides 600 mM norepinephrine in 70:0:30 delivery vehicle and also satisfies this criteria.

Significantly, after a long succession of in-depth screening and experimentation acceptable formulations were identified to satisfy each of the criteria i) through vi) listed above. A delivery vehicle comprising EtOH and water in a ratio of 70:30 was effective. Compositions comprising norepinephrine at about 450 mM to about 750 mM were also effective. Preferred formulations comprise between 500-700 mM norepinephrine. Still more preferred are formulations comprising about 550-650 mM norepinephrine. In a presently preferred embodiment, 600 mM norepinephrine-tartrate dissolved in 70% ethanol plus 30% water was found to satisfy the above criteria and deliver the vasoconstrictor to the intradermal vasculature of keratinized skin or scalp tissue.

The skilled artisan will appreciate that the examples and the description provided herein serve to further describe aspects of the invention, which can be varied and adapted while still remaining within the scope of the appended claims.

What is claimed is:

1. A method for reducing at least one condition of radiation-induced or chemotherapy-induced, dermatitis, gastrointestinal distress, or proctitis comprising topically administering to a patient treated or to be treated with a chemotherapeutic agent, radiation therapy, or a combination thereof a preparation comprising a vasoconstrictor comprising epinephrine, phenylephrine, methoxamine, norepinephrine, zolmitriptan, tetrahydrozoline, naphazoline, oxidesumitriptan, avitriptan, rizatriptan, almotriptan, frovatriptan, or a combination thereof, in a pharmaceutically-acceptable, water-soluble alcohol-containing delivery vehicle in an amount effective to reduce the at least one condition.

2. The method of claim 1 wherein said condition is reduced in one or more non-neoplastic cells of the skin, rectum, gastrointestinal system, or urogenital system.

3. The method of claim 1 wherein the vasoconstrictor is selected so as to minimize risk of undesirable cardiac side-effects.

4. The method of claim 1 wherein the administering step is performed prior to treatment with the chemotherapeutic agent, radiation therapy, or the combination thereof.

5. The method of claim 4 wherein the condition is radiation-induced dermatitis, and the preparation comprises norepinephrine in a topical delivery vehicle for delivering the vasoconstrictor to cells within the skin.

6. The method of claim 5, wherein the topical delivery system comprises at least 50% alcohol.

7. The method of claim 5, wherein the alcohol comprises ethanol, propylene glycol, or a combination thereof.

8. The method of claim 7, wherein the topical delivery system comprises between about 50% and about 75% ethanol, between about 25% and 45% water, and balance propylene glycol.

9. The method of claim 5, wherein the preparation comprises between about 100 mM and 1500 mM norepinephrine.

10. The method of claim 5, wherein the preparation comprises between about 200 mM and 800 mM norepinephrine.

11. The method of claim 5, wherein the preparation comprises between about 450 mM and 750 mM norepinephine.

12. The method of claim 5, wherein the administering step is performed prior to treatment with the chemotherapeutic agent, the radiation therapy, or the combination thereof.

13. The method of claim 4 wherein the condition is gastrointestinal distress and the preparation allows for delivering the vasoconstrictor to cells within the esophagus, stomach, or intestines.

14. The method of claim 13, wherein the preparation comprises a gel, a mucoadhesive coating, or a foam preparation.

15. The method of claim 4 wherein the condition is proctitis, and the preparation comprises a vasoconstrictor in a topical delivery vehicle for delivering the vasoconstrictor to cells within the rectum.

16. The method of claim 15 wherein the preparation comprises a gel, a mucoadhesive coating, a suppository, or a foam preparation.

17. The method of claim 15 wherein the therapy is radiation therapy, and the method further comprises administering after the radiation therapy, an effective amount of a preparation comprising an a1 adrenergic receptor antagonist in a pharmaceutically-acceptable delivery vehicle for delivering the vasoconstrictor to cells within the rectum.

18. The method of claim 17 wherein the pharmaceutically-acceptable delivery vehicle is a topical delivery vehicle which is moisturizing, or lubricating.

19. The method according to claim 1 wherein said preparation is topically administered to a patient treated or to be treated with a chemotherapeutic agent.

20. A method of delivering a vasoconstrictor to squamous tissue in a subject comprising:
topically administering to the subject a composition comprising a vasoconstrictor comprising one or more of epinephrine, phenylephrine, methoxamine, norepinephrine, zolmitriptan, tetrahydrozoline, naphazoline, oxidesumitriptan, avitriptan, rizatriptan, almotriptan, or frovatriptan in a pharmaceutically-acceptable delivery vehicle wherein said vehicle comprises water and at least 50% or about 50% ethanol and is specifically formulated to allow vasoconstrictor penetration of the squamous tissue; and treating said subject with chemotherapy, radiation therapy, or both, prior to the topical administration, during the topical administration, or following the topical administration.

21. The method of claim 20 wherein the composition delivers the vasoconstrictor to the underlying dermal vasculature that serves epidermal and hair follicle stem cells.

22. The method of claim 20 wherein the vehicle allows penetration of the stratum corneum or hair follicle sebum residue.

23. The method of claim 20 wherein the vasoconstrictor comprises norepinephrine.

24. The method of claim 23 wherein the norepinephrine is present at concentration of about 200-800 mM.

25. The method of claim 20 wherein the ethanol and water are in a ratio of 70:30.

26. A method for reducing at least one condition of radiation-induced or chemotherapy-induced alopecia or dermatitis comprising topically administering to a patient treated or to be treated with a chemotherapeutic agent, radiation therapy, or a combination thereof a preparation comprising a vasoconstrictor comprising epinephrine, phenylephrine, methoxamine, norepinephrine, zolmitriptan, tetrahydrozoline, naphazoline, oxidesumitriptan, avitriptan, rizatriptan, almotriptan, frovatriptan, or a combination thereof in an amount effective to reduce said mucositis and in a pharmaceutically-acceptable delivery vehicle comprising water and at least 50% or about 50% ethanol.

27. The method according to claim 26 wherein said pharmaceutically-acceptable delivery vehicle comprises between about 50% and about 75% ethanol.

28. The method according to claim 26 wherein said preparation comprises between about 100 mM and 1500 mM norepinephrine.

29. The method according to claim 26 wherein said preparation is topically administered to a patient treated or to be treated with a chemotherapeutic agent.

30. A method for reducing at least one condition of radiation-induced or chemotherapy-induced mucositis comprising topically administering to a patient treated or to be treated with a chemotherapeutic agent, radiation therapy, or a combination thereof a preparation comprising a vasoconstrictor comprising epinephrine, phenylephrine, methoxamine, norepinephrine, zolmitriptan, tetrahydrozoline, naphazoline, oxidesumitriptan, avitriptan, rizatriptan, almotriptan, frovatriptan, or a combination thereof in an amount effective to reduce said mucositis and in a pharmaceutically-acceptable delivery vehicle comprising ethanol and propylene glycol.

31. The method according to claim 30 wherein said preparation comprises phenylephrine.

32. The method according to claim 30 wherein said preparation comprises 5% ethanol.

33. The method according to claim 30 wherein said preparation comprises ethanol, propylene glycol, and glycerol.

34. The method according to claim 30 wherein said preparation is topically administered to a patient treated or to be treated with a chemotherapeutic agent.

35. A method of delivering a vasoconstrictor to squamous tissue in a subject comprising:

topically administering to the subject a composition comprising a vasoconstrictor comprising one or more of epinephrine, phenylephrine, methoxamine, norepinephrine, zolmitriptan, tetrahydrozoline, naphazoline, oxidesumitriptan, avitriptan, rizatriptan, almotriptan, or frovatriptan in a pharmaceutically-acceptable delivery vehicle wherein said vehicle comprises ethanol and propylene glycol and is specifically formulated to allow vasoconstrictor penetration of the squamous tissue; and treating said subject with chemotherapy, radiation therapy, or both, prior to the topical administration, during the topical administration, or following the topical administration.

36. The method according to claim 35 wherein said preparation comprises phenylephrine.

37. The method according to claim 35 wherein said preparation comprises 5% ethanol.

38. The method according to claim 35 wherein said preparation comprises ethanol, propylene glycol, and glycerol.

39. The method according to claim 35 wherein said preparation is topically administered to a patient treated or to be treated with a chemotherapeutic agent.

* * * * *

UNITED STATES PATENT AND TRADEMARK OFFICE
CERTIFICATE OF CORRECTION

PATENT NO.      : 8,114,914 B2
APPLICATION NO. : 11/471047
DATED           : February 14, 2012
INVENTOR(S)     : William E. Fahl, Arnold E. Ruoho and Minesh Mehta It is certified that error appears in the above-identified patent and that said Letters Patent is hereby corrected as shown below:

At column 32, line 51, please delete "al" and insert therefor --αl--

At column 33, line 22, please delete "alopecia or dermatitis" and insert therefor --mucositis--

Signed and Sealed this
Sixteenth Day of October, 2012

David J. Kappos
*Director of the United States Patent and Trademark Office*